(12) United States Patent     (10) Patent No.:    US 8,058,514 B2
Ishida et al.     (45) Date of Patent:    Nov. 15, 2011

(54) AGROBACTERIUM-MEDIATED METHOD FOR PRODUCING TRANSFORMED PLANT WITHOUT SELECTION STEP

(75) Inventors: Yuji Ishida, Iwata (JP); Yukoh Hiei, Iwata (JP)

(73) Assignee: Japan Tobacco Inc., Tokyo (JP)

( * ) Notice: Subject to any disclaimer, the term of this patent is extended or adjusted under 35 U.S.C. 154(b) by 0 days.

(21) Appl. No.: 12/528,985

(22) PCT Filed: Feb. 28, 2008

(86) PCT No.: PCT/JP2008/053559
§ 371 (c)(1),
(2), (4) Date: Aug. 27, 2009

(87) PCT Pub. No.: WO2008/105509
PCT Pub. Date: Sep. 4, 2008

(65) Prior Publication Data
US 2010/0132066 A1    May 27, 2010

(30) Foreign Application Priority Data
Feb. 28, 2007    (JP) ................................ 2007-049172

(51) Int. Cl.
*A01H 1/00* (2006.01)
*C12N 15/82* (2006.01)

(52) U.S. Cl. ....................... 800/294; 800/320.1; 435/469

(58) Field of Classification Search .................. 435/469; 800/294, 320.1, 300.1
See application file for complete search history.

(56) References Cited

U.S. PATENT DOCUMENTS

| 2005/0097641 A1* | 5/2005 | Wolters et al. ................. 800/294 |
| 2006/0260012 A1* | 11/2006 | Khan ............................ 800/287 |
| 2011/0030100 A1 | 2/2011 | Hiei et al. |

FOREIGN PATENT DOCUMENTS

| EP | 1 306 441 A1 | 5/2003 |
| EP | 1306441 A1 * | 5/2003 |
| EP | 1662002 A1 | 5/2006 |
| EP | 1669444 A1 | 6/2006 |
| JP | 2000-23675 A | 1/2000 |
| JP | 2000-342253 A | 12/2000 |
| JP | 2000-342255 A | 12/2000 |
| JP | 2000-342256 A | 12/2000 |
| WO | WO 02/12520 A1 | 2/2002 |
| WO | WO 2005/017152 A1 | 2/2005 |
| WO | WO 2005/017169 A1 | 2/2005 |
| WO | WO 2006/122023 A1 | 11/2006 |

OTHER PUBLICATIONS

Frame et al. Improved Agrobacterium-mediated transformation of three maize inbred lines using MS salts. Plant Cell Rep. (2006) 25:1024-1034.*

Trifonova et al. Agrobacterium-mediated transgene delivery and integration into barley under a range of in vitro culture conditions. Plant Science 161 (2001) 871-880.*

Agarwal et al. Comparison of genetic transformation in *Morus alba* L. via different regeneration systems. Plant Cell Rep (2007) 26:177-185.*

Frame et al., "Improved Agrobacterium-mediated transformation of three maize inbred lines using MS salts", Genetic Transformation and Hybridization, Plant Cell Rep, (2006), vol. 25, pp. 1024-1034.

Trifonova et al., "Agrobacterium-mediated transgene delivery and integration into barley under a range of in vitro culture conditions", Plant Science, vol. 161, pp. 871-880, 2001.

Hiei et al., "Improved protocols for transformation of indica rice mediated by *Agrobacterium tumefaciens*", Plant Cells, Tissue and Organ Culture, (2006), vol. 85, pp. 271-283.

Agarwal et al., "Comparison of genetic transformation in *Morus alba* L. via different regeneration systems," Plant Cell Reports, vol. 26, No. 2, Sep. 2006, pp. 177-185 (Abstract only provided).

Akula et al., "Improved regeneration efficiency from mature embryos of barley cultivars," Biologia Plantarum, vol. 42, No. 4, 1999, pp. 505-513.

Chan et al., "Agrobacterium-mediated production of transgenic rice plants expressing a chimeric α-amylase promoter/β-glucuronidase gene," Plant Molecular Biology, vol. 22, 1993, pp. 491-506.

Cheng et al., "Genetic Transformation of Wheat Mediated by *Agrobacterium tumefaciens*," Plant Physiol., vol. 115, 1997, pp. 971-980.

Chu, "The N6 Medium and its Applications to Anther Culture of Cereal Crops," Proceedings of Symposium on Plant Tissue Culture, Peking, Pitman Publishing Ltd. and The Science Press, Aug. 1978, pp. 43-50.

Cui et al., "A rapid Agrobacterium-mediated transformation of *Antirrhinum majus* L. by using direct shoot regeneration from hypocotyl explants," Plant Science, vol. 166, 2004, pp. 873-879.

De Cleene et al., "The Host Range of Crown Gall," The Botanical Review, vol. 42, No. 4, Oct.-Dec. 1976, pp. 389-466. Deji et al., "Genomic organization and transcriptional regulation of maize ZmRR1 and ZmRR2 encoding cytokinin-inducible response regulators," Biochimica et Biophysica Acta, vol. 1492, 2000, pp. 216-220.

Extended European Search Report, dated May 31, 2010, for European Application No. 08721008.4.

Frame et al., "*Agrobacterium tumefaciens*-Mediated Transformation of Maize Embryos Using a Standard Binary Vector System," Plant Physiology, vol. 129, May 2002, pp. 13-22.

Gould et al., "Transformation of *Zea mays* L. Using *Agrobacterium tumefaciens* and the Shoot Apex," Plant Physiol., vol. 95, 1991, pp. 426-434.

Grimsley et al., "Agrobacterium-mediated delivery of infectious maize streak virus into maize plants," Nature, vol. 325, Jan. 8, 1987, pp. 177-179.

(Continued)

*Primary Examiner* — June Hwu
(74) *Attorney, Agent, or Firm* — Birch, Stewart, Kolasch & Birch, LLP

(57) ABSTRACT

A novel *Agrobacterium*-mediated method for producing a transformed monocotyledonous plant is provided. The transformation method involves (i) a coculture step for culturing an *Agrobacterium*-inoculated monocotyledonous plant tissue with a coculture medium containing 3,6-dichloro-o-anisic acid, 4-amino-3,5,6-trichloropicolinic acid and/or 2,4,5-trichlorophenoxyacetic acid, and (ii) a regeneration step for culturing the tissue obtained in (i) with a regeneration medium containing a selective drug to thereby induce regeneration and to produce a transformed plant. The method does not include, between the coculture step and the regeneration step, any selection step for culturing the cocultured tissue with a medium containing an auxin and a selective drug to select a transformant.

6 Claims, 4 Drawing Sheets

OTHER PUBLICATIONS

Grimsley et al., "DNA Transfer from Agrobacterium to *Zea mays* or Brassica by agroinfection is dependent on bacterial virulence functions," Mol. Gen. Genet., vol. 217, 1989, pp. 309-316.

Grimsley et al., "Meristematic Tissues of Maize Plants Are Most Susceptible To Agroinfection With Maize Streak Virus," Bio/Technology, vol. 6, Feb. 1988, pp. 185-189.

Hiei et al., "Efficient transformation of rice (*Oryza sativa* L.) mediated by Agrobacterium and sequence analysis of the boundaries of the T-DNA," The Plant Journal, vol. 6, No. 2, 1994, pp. 271-282.

Huang et al., "Successful Agrobacterium-mediated genetic transformation of maize elite inbred lines," Plant Cell, Tissue and Organ Culture, vol. 83, 2005, pp. 187-200.

Ishida et al., "High efficiency transformation of maize (*Zea mays* L.) mediated by *Agrobacterium tumefaciens*," Nature Biotechnology, vol. 14, Jun. 1996, pp. 745-750.

Ishida et al., "Improved Protocol for Transformation of Maize (*Zea mays* L.) Mediated by *Agrobacterium tumefaciens*," Plant Biotechnology, vol. 20, No. 1, 2003, pp. 57-66.

Komari et al., "Efficient selection of somatic hybrids in *Nicotiana tabacum* L. using a combination of drug resistance markers introduced by transformation," Theor. Appl. Genet., vol. 77, 1989, pp. 547-552.

Komari et al., "Vectors carrying two separate T-DNAs for co-transformation of higher plants mediated by *Agrobacterium tumefaciens* and segregation of transformants free from selection markers," The Plant Journal, vol. 10, No. 1, 1996, pp. 165-174.

Linsmaier et al., "Organic Growth Factor Requirements of Tobacco Tissue Cultures," Physiologia Plantarum, vol. 18, 1965, pp. 100-127.

Mooney et al., "Agrobacterium tumefaciens-gene transfer into wheat tissues," Plant Cell, Tissue and Organ Culture, vol. 25, 1991, pp. 209-218.

Negrotto et al., "The use of phosphomannose-isomerase as a selectable marker to recover transgenic maize plants (*Zea mays* L.) via Agrobacterium transformation," Plant Cell Reports, vol. 19, 2000, pp. 798-803.

Nishiguchi et al., "An improved transformation system for Lombardy poplar (*Populus nigra* var. italica)," J. For. Res., vol. 11, 2006, pp. 175-180.

Nomura et al., "The evolution of C4 plants: acquisition of cis-regulatory sequences in the promoter of C4-type pyruvate, orthophosphate dikinase gene," The Plant Journal, vol. 22, No. 3, 2000, pp. 211-221.

Nomura et al., "The promoter of rbcS in a C3 plant (rice) directs organ-specific, light-dependent expression in a C4 plant (maize), but does not confer bundle sheath cell-specific expression," Plant Molecular Biology, vol. 44, 2000, pp. 99-106.

Potrykus, "Gene transfer to cereals: an Assessment," Bio/Technology, vol. 8, Jun. 1990, pp. 535-542.

Raineri et al., "Agrobacterium-Mediated Transformation of Rice (*Oryza sativa* L.)," Bio/Technology, vol. 8, Jan. 1990, pp. 33-38.

Sambrook et al., "Molecular Cloning: A Laboratory Manual, Second Edition," Cold Spring Harbor Laboratory Press, Cold Spring Harbor, NY, 1989, pp. 9.31-9.62.

Taniguchi et al., "The Promoter for the Maize C4 Pyruvate, orthophosphate Dikinase Gene Directs Cell- and Tissue-Specific Transcription in Transgenic Maize Plants," Plant Cell Physiol., vol. 41, No. 1, 2000, pp. 42-48.

Tingay et al., "*Agrobacterium tumefaciens*-mediated barley transformation," The Plant Journal, vol. 11, No. 6, 1997, pp. 1369-1376.

Toki et al., "Early infection of scutellum tissue with Agrobacterium allows high-speed transformation of rice," The Plant Journal, vol. 47, 2006, pp. 969-976.

Watson et al., "Plasmid Required for Virulence of *Agrobacterium tumefaciens*," Journal of Bacteriology, vol. 123, No. 1, Jul. 1975, pp. 255-264.

Zhang et al., "Cre/lox-mediated marker gene excision in transgenic maize (*Zea mays* L.) plants," Theor. Appl. Genet., vol. 107, 2003, pp. 1157-1168.

Zhao et al., "Agrobacterium-mediated sorghum transformation," Plant Molecular Biology, vol. 44, 2000, pp. 789-798.

Zhao et al., "High throughput genetic transformation mediated by *Agrobacterium tumefaciens* in maize," Molecular Breeding, vol. 8, 2001, pp. 323-333.

\* cited by examiner

AGROBACTERIUM-MEDIATED METHOD FOR PRODUCING TRANSFORMED PLANT WITHOUT SELECTION STEP

TECHNICAL FIELD

The present application claims priority to Japanese Patent Application No. 2007-49172 filed on Feb. 28, 2007.

The present invention relates to a novel *Agrobacterium*-mediated method for producing a transformed plant.

BACKGROUND ART

Methods previously known for transformation of monocotyledons such as maize and rice, which are major grain crops, include electroporation, particle gun transformation, etc. However, these physical gene transfer methods have problems in that genes are introduced as multiple copies or are not inserted in an intact state, and the resulting transformed plants may often develop malformations and sterility.

*Agrobacterium*-mediated gene transfer is universally used as a transformation method for dicotyledons. Although it has been understood that hosts of *Agrobacterium* are limited only to dicotyledons and *Agrobacterium* has no ability to infect monocotyledons (Non-patent Publication No. 1), some attempts have been made to transform monocotyledons through *Agrobacterium*-mediated method.

Grimsley et al. have reported that when maize streak virus DNA was inserted into T-DNA of *Agrobacterium* and inoculated into maize growing points, infection with maize streak virus was confirmed. Since such infection symptoms are not observed simply when the maize streak virus DNA alone is inoculated, Grimsley et al. have recognized that the above observation indicates the ability of *Agrobacterium* to introduce DNA into maize (Non-patent Publication No. 2). However, this result is not indicative of T-DNA integration into nuclei, because a virus will multiply even when not integrated into a nuclear genome. Grimsley et al. have further demonstrated that the highest infection efficiency is observed upon inoculation into a growing point in the shoot apex of maize (Non-patent Publication No. 3), and that the VirC gene in plasmids of *Agrobacterium* is essential for infection (Non-patent Publication No. 4).

Gould et al. injured maize growing points with a needle and then inoculated these growing points with super-virulent *Agrobacterium* EHA1 carrying the kanamycin resistance gene and the GUS gene, followed by kanamycin selection on the treated growing points to obtain a resistant plant. Upon Southern analysis to confirm whether progeny seeds of this plant have the introduced gene, they confirmed that some seeds had the transgene (Non-patent Publication No. 5). This indicates that the whole plant obtained by kanamycin selection on *Agrobacterium*-treated growing points had both transformed and non-transformed cells (chimerism).

Mooney et al. attempted to introduce the kanamycin resistance gene into wheat embryos by using *Agrobacterium*. First, the embryos were enzymatically treated to injure their cell walls, and then inoculated with *Agrobacterium*. Among the treated calli, very few calli were grown that appeared to be resistant to kanamycin, but no whole plant was regenerated from these calli. Upon Southern analysis to confirm the presence of the kanamycin resistance gene, all the resistant calli were found to have a structural mutation in the transgene (Non-patent Publication No. 6).

Raineri et al. performed super-virulent *Agrobacterium* A281 (pTiBo542) treatment on 8 varieties of rice whose embryonic disc had been injured, and they confirmed tumorous tissue growth in 2 varieties of Nipponbare, Fujisaka 5. Further, when rice embryos were inoculated with *Agrobacterium* carrying a Ti plasmid modified to have the kanamycin resistance gene and the GUS gene wherein hormone synthesis genes in T-DNA have been removed, the growth of kanamycin-resistant calli was observed. In these resistant calli, GUS gene expression was observed, but no transformed plant was obtained. Based on these results, Raineri et al. have recognized that the *Agrobacterium* T-DNA was introduced into rice cells (Non-patent Publication No. 7).

As shown above, there are study reports suggesting that *Agrobacterium*-mediated gene transfer is also possible for Gramineae crops including rice, maize and wheat, but these reports failed to show persuasive results because these studies had a problem in reproducibility and were also insufficient for transgene confirmation (Non-patent Publication No. 8).

Chan et al. injured immature rice embryos, which had been cultured for 2 days in the presence of 2,4-D, and then inoculated these embryos with *Agrobacterium* carrying genes for npt II and GUS in a medium containing suspension-cultured potato cells. They cultured the thus treated immature embryos on a G418-containing medium to obtain regenerated plants from the induced calli. They confirmed the location of the GUS gene in the regenerated plants and their progeny plants by Southern analysis, and reported that the presence of the transgene was observed in plants of both $R_0$ and $R_1$ generations (Non-patent Publication No. 9). This result supports *Agrobacterium*-mediated transformation in rice, but the transformation efficiency was as low as 1.6%. Moreover, there was only one regenerated plant that showed normal growth, although 250 immature embryos were used for testing. Since enormous efforts are required to extract immature embryos of rice, such low transformation efficiency is not practical.

In recent years, it has been reported that stable and highly efficient transformation is also possible in monocotyledons including rice and maize when using a super-binary vector carrying a part of the virulence gene from super-virulent *Agrobacterium* (Non-patent Publications No. 10 and 11). These reports suggest that *Agrobacterium*-mediated transformation not only allows stable and highly efficient transformation, but is also advantageous in that the resulting transformed plants have fewer mutations, and in that the introduced genes are low in copy number and are often in an intact state. Following success in rice and maize, further reports were issued for *Agrobacterium*-mediated transformation in other major grain crops, i.e., wheat (Non-patent Publication No. 12), barley (Non-patent Publication No. 13) and sorghum (Non-patent Publication No. 14).

Ishida et al. (1996) (Non-patent Publication No. 11) used maize inbred lines as materials to perform *Agrobacterium*-mediated transformation. Thereafter, further reports were issued for *Agrobacterium*-mediated transformation in maize (Non-patent Publications No. 15-21). Attempts which have been made to improve the efficiency of *Agrobacterium*-mediated maize transformation include: selection of transformed cells on N6 basal medium (Non-patent Publication No. 21); addition of $AgNO_3$ and carbenicillin to culture medium (Non-patent Publications No 20 and 22); and addition of cysteine to coculture medium (Non-patent Publication No. 21). Ishida et al. (2003) (Non-patent Publication No. 22) have reported that the transformation efficiency in maize is improved when cocultured immature maize embryos are selected on a medium containing $AgNO_3$ and carbenicillin.

As shown above, in the case of *Agrobacterium*-mediated maize transformation, modifications to the medium composition or selection marker genes also result in improved efficiency and an extended range of varieties to be applied. However, in almost all the methods previously reported for Agrobacterium-mediated maize transformation, a transformed plant is obtained through the steps of inducing a callus from an inoculated immature embryo, allowing a transformed callus to selectively grow on a medium containing a herbicide component or an antibiotic, and placing the resulting transformed cell aggregate onto a regeneration medium (Non-patent Publications No. 15-21, 23 and 24). In some reports, tissue culture in a dedifferentiated state (callus) extends over a long period of time, more than 2 months (Non-patent Publications No. 20 and 25). Since long-term subculture in a dedifferentiated state is more likely to cause somatic cell mutations, if it is possible to obtain a regenerated plant within a minimum period of time, the resulting transformed plant can be expected to remain in a state closer to its original variety, which provides a great merit in conducting test studies and/or new variety breeding. Moreover, techniques enabling the production of transformed plants within a short period of time contribute to efficient implementation of test studies and/or new variety breeding.

Further, when performing a selection step on dedifferentiated tissues, it is necessary to excise a drug-resistant and good-shaped callus under a microscope with a surgical knife and a pair of tweezers, and then place this callus onto a fresh selective medium and a regeneration medium. Such manipulations are complicated and time-consuming, and also require a great deal of skill in selecting a good-shaped callus. Such a selection step on a selective medium extends over a long period of time and involves complicated manipulations. Moreover, culture in an undifferentiated state is more likely to cause mutations. Despite these demerits, the selection step is regarded as essential for obtaining a transformed whole plant.

In planta transformation used in *Arabidopsis* is a technique that can be expected to cause fewer mutations because it does not involve any culture step. However, this technique is difficult to apply in monocotyledons such as maize and rice. On the other hand, there is also a report on the production of transformed plant through *Agrobacterium* inoculation into a shoot apex tissue. However, such a technique has problems in efficiency and reproducibility, and hence is not practical.

Recently, a method has been reported, in which rice mature seeds cultured for one day in a medium containing 2,4-D are inoculation with *Agrobacterium* to thereby obtain a transformed plant within one month after inoculation (Non-patent Publication No. 26). However, this method also involves a step for tissue selection in a dedifferentiated state over 2 weeks.

Patent Publication No. 1: JP 2000-342255 A
Patent Publication No. 2: JP 2000-342256 A
Patent Publication No. 3: JP 2000-23675 A
Patent Publication No. 4: JP 2000-342253 A
Patent Publication No. 5: WO2005/017169
Patent Publication No. 6: WO2005/017152
Non-patent Publication No. 1: De Cleene, M. and De Ley, J. (1976) The host range of crown gall. Bot. Rev. 42:389-466.
Non-patent Publication No. 2: Grimsley, N., Horn, T., Davis, J. W. and Horn, B. (1987) *Agrobacterium*-mediated delivery of infectious maize streak virus into maize plants. Nature 325:177-179.
Non-patent Publication No. 3: Grimsley, N. H., Ramos, C., Hein, T. and Horn, B. (1988) Meristematic tissues of maize plants are most susceptible to Agroinfection with maize streak virus. Bio/technology 6:185-189.
Non-patent Publication No. 4: Grimsley, N., Horn, B., Ramos, C., Kado, C. and Rogowsky, P. (1989) DNA transfer from *Agrobacterium* to *Zea mays* or *Brassica* by agroinfection is dependent on bacterial virulence functions. Mol. Gen. Genet. 217:309-316.
Non-patent Publication No. 5: Gould, J., Devey, M., Hasegawa, O., Ulian, E. C., Peterson, G. and Smith, R. H. (1991) Transformation of *Zea mays* L. using *Agrobacterium tumefaciens* and shoot apex. Plant Physiol. 95:426-434.
Non-patent Publication No. 6: Mooney, P. A., Goodwin, P. B., Dennis, P. S. and Llewellyn, D. J. (1991) *Agrobacterium tumefaciens*-gene transfer into wheat tissues. Plant Cell, Tissues and Organ Culture 25:209-218.
Non-patent Publication No. 7: Raineri, D. M., Bottino, P., Gordon, M. P. and Nester, E. W. (1990) *Agrobacterium*-mediated transformation of rice (*Oryza sativa* L.). Bio/technology 8:33-38.
Non-patent Publication No. 8: Potrycus, I (1990) Gene transfer to cereals: an assessment. Bio/technology 8:535-542.
Non-patent Publication No. 9: Chan, M-T., Chang, H-H., Ho, S-L., Tong, W-F. and Yu, S-M. (1993) *Agrobacterium*-mediated production of transgenic rice plants expressing a chimeric α-amylase promoter/β-glucuronidase gene. Plant Mol. Biol. 22:491-506.
Non-patent Publication No. 10: Hiei, Y., Ohta, S., Komari, T. and Kumashiro, T. (1994) Efficient transformation of rice (*Oryza sativa* L.) mediated by *Agrobacterium* and sequence analysis of the boundaries of the T-DNA. The Plant Journal 6:271-282.
Non-patent Publication No. Ishida, Y., Saito, H., Ohta, S., Hiei, Y., Komari, T. and Kumashiro, T. (1996) High efficiency transformation of maize (*Zea mays* L.) mediated by *Agrobacterium tumefaciens*. Nature Biotechnology 14:745-750.
Non-patent Publication No. 12: Cheng, M., Fry, J. E., Pang, S., Zhou, H., Hironaka, C. M., Duncan, D. R., Conner, T. W., Wan, Y. (1997) Genetic transformation of wheat mediated by *Agrobacterium tumefaciens*. Plant Physiol. 115: 971-980.
Non-patent Publication No. 13: Tingay, S., McElroy, D., Kalla, R., Fieg, S., Wang, M., Thornton, S., Brettell, R. (1997) *Agrobacterium tumefaciens*-mediated barley transformation. Plant J. 11: 1369-1376.
Non-patent Publication No. 14: Zhao, Z.-Y., Cai, T., Tagliani, L., Miller, M., Wang, N., Peng, H., Rudert, M., Schoeder, S., Hondred, D., Seltzer, J., Pierce, D. (2000) *Agrobacterium*-mediated sorghum transformation. Plant Mol. Biol. 44: 789-798.
Non-patent Publication No. 15: Deji, A., Sakakibara, H., Ishida, Y., Yamada, S., Komari, T., Kubo, T., Sugiyama, T. (2000) Genomic organization and transcriptional regulation of maize ZmRR1 and ZmRR2 encoding cytokinin-inducible response regulators. Biochim et Biophys. Acta 1492: 216-220.
Non-patent Publication No. 16: Negrotto, D., Jolley, M., Beer, S., Wenck, A. R., Hansen, G. (2000) The use of phosphomannose-isomerase as a selection marker to recover transgenic maize plants (*Zea mays* L.) via *Agrobacterium* transformation. Plant Cell Reports 19: 798-803.
Non-patent Publication No. 17: Nomura, M., Sentoku, N., Nishimura, A., Lin, J-H., Honda, C., Taniguchi, M., Ishida, Y., Ohta, S., Komari, T., Miyao-Tokumori, M., Kono-Murakami, Y., Tajima, S., Ku, M. S. B., Matsuoka, M. (2000a) The evolution of C4 plants: acquisition of cis-regulatory sequences in the promoter of C4-type pyruvate, orthophosphate dikinase gene. Plant J. 22: 211-221.
Non-patent Publication No. 18: Nomura, M., Katayama, K., Nishimura, A., Ishida, Y., Ohta, S., Komari, T., Miyao- Tokutomi, M., Tajima, S., Matsuoka, M. (2000b) The promoter of rbcS in a C3 plant (rice) directs organ-specific, light-dependent expression in a C4 plant (maize), but does not confer bundle sheath cell-specific expression. Plant Mol. Biol. 44: 99-106.

Non-patent Publication No. 19: Taniguchi, M., Izawa, K., Ku, M. S. B., Lin, J-H., Saito, H., Ishida, Y., Ohta, S., Komari, T., Matsuoka, M., Sugiyama, T. (2000) The promoter for the maize $C_4$ pyruvate, orthophosphate dikinase gene directs cell- and tissue-specific transcription in transgenic maize plants. Plant Cell Physiol. 41: 42-48.

Non-patent Publication No. 20: Zhao, Z.-Y., Gu, W., Cai, T., Tagliani, L., Hondred, D., Bond, D., Schroeder, S., Rudert, M., Pierce, D. (2001) High throughput genetic transformation mediated by *Agrobacterium tumefaciens* in maize. Mol. Breed. 8: 323-333.

Non-patent Publication No. 21: Frame, B. R., Shou, H., Chikwamba, R. K., Zhang, Z., Xiang, C., Fonger, T. M., Pegg, S. E. K., Li, B., Nettleton, D. S., Pei, D., Wang, K. (2002) *Agrobacterium tumefaciens*-mediated transformation of maize embryos using a standard binary vector system. Plant Physiol. 129: 13-22.

Non-patent Publication No. 22: Ishida, Y., Saito, H., Hiei, Y., Komari, T. (2003) Improved protocol for transformation of maize (*Zea mays L.*) mediated by *Agrobacterium tumefaciens*. Plant Biotechnology 20:57-66.

Non-patent Publication No. 23: Zhang, W., Subbarao, S., Addae, P., Shen, A., Armstrong, C., Peschke, V., Gilbertson, L. (2003) Cre/lox-mediated marker gene excision in transgenic maize (*Zea mays L.*) plants. Theor. Appl. Genet. 107: 1157-1168.

Non-patent Publication No. 24: Frame, B. R., McMurray, J. M., Fonger, T. M., Main, M. L., Taylor, K. W., Torney, F. J., Paz, M. M., Wang, K. (2006) Improved *Agrobacterium*-mediated transformation of three maize inbred lines using MS salts. Plant Cell Rep. 25: 1024-1034.

Non-patent Publication No. 25: Huang, X. and Wei, Z. (2005) Successful *Agrobacterium*-mediated genetic transformation of maize elite inbred lines. Plant Cell, Tissue and Organ Culture 83:187-200.

Non-patent Publication No. 26: Toki, S., Hara, N., Ono, K., Onodera, H., Tagiri, A., Oka, S., Tanaka, H. (2006) Early infection of scutellum tissue with *Agrobacterium* allows high-speed transformation of rice. The Plant Journal 47:969-976.

Non-patent Publication No. 27: Hiei, Y. and Komari, T. (2006) Improved protocols for transformation of indica rice mediated by *Agrobacterium tumefaciens*. Plant Cell, Tissue and Organ Culture 85:271-283.

Non-patent Publication No. 28: Komari, T., Hiei, Y., Saito, Y., Murai, N., Kumashiro, T. (1996) Vectors carrying two separate T-DNAs for co-transformation of higher plants mediated by *Agrobacterium tumefaciens* and segregation of transformants free from selection markers. The Plant Journal 10:165-174.

Non-patent Publication No. 29: Komari, T., Saito, Y., Nakakido, F., Kumashiro, T. (1989) Efficient selection of somatic hybrids in *Nicotiana tabacum L.* using a combination of drug-resistance merkers introduced by transformation. Theor. Appl. Genet. 77:547-552.

Non-patent Publication No. 30: Sambrook, J., Fritsch, E. F., Maniatis, T. (1989) Molecular Cloning: A Laboratory Manual, 2nd ed., Cold Spring Harbor Laboratory Press, Cold Spring Harbor, N.Y.

Non-patent Publication No. 31: Watson, B., Currier, T. C., Gordon, M. P., Chilton, M.-D. and Nester, E. W. (1975) Plasmid required for virulence of *Agrobacterium tumefaciens*. J Bacteriol, 123, 255-264.

Non-patent Publication No. 32: Linsmaier, E., Skoog, F. (1965) Organic growth factor requirements of tobacco tissue culture. Physiol. Plant. 18:100-127.

Non-patent Publication No. 33: Chu, C.-C. (1978) The N6 medium and its applications to anther culture of cereal crops. In: Proc. Symp. Plant Tissue Culture. Peking: Science Press, pp 43-50.

DISCLOSURE OF THE INVENTION

Problems to be Solved by the Invention

The object of the present invention is to provide a novel *Agrobacterium*-mediated method for producing a transformed plant.

Means for Solving the Problems

As a result of extensive and intensive efforts made to solve the problems stated above, the inventors of the present invention have found that when an *Agrobacterium*-inoculated plant tissue is cultured with a coculture medium containing 3,6-dichloro-o-anisic acid (dicamba), 4-amino-3,5,6-trichloropicolinic acid (picloram) and/or 2,4,5-trichlorophenoxyacetic acid (2,4,5-T), the above plant tissue has the regeneration rate and vigor that are sufficient to obtain a transformed whole plant, even if the selection step conventionally required is eliminated and a regeneration step is performed directly. This finding led to the completion of the present invention. The present invention is preferably accomplished by, but is not limited to, the embodiments shown below.

The present invention provides a method for producing a transformed plant, which comprises (i) a coculture step for culturing an *Agrobacterium*-inoculated plant tissue with a coculture medium containing 3,6-dichloro-o-anisic acid, 4-amino-3,5,6-trichloropicolinic acid and/or 2,4,5-trichlorophenoxyacetic acid, and (ii) a regeneration step for culturing the tissue obtained in (i) with a regeneration medium containing a selective drug to thereby induce regeneration, wherein said method does not comprise, between the coculture step and the regeneration step, any selection step for culturing the cocultured tissue with an auxin-containing medium to select a transformant by drug selection.

In a preferred embodiment of the present invention, the coculture medium is free from any auxin member other than 3,6-dichloro-o-anisic acid, 4-amino-3,5,6-trichloropicolinic acid and 2,4,5-trichlorophenoxyacetic acid.

In a more preferred embodiment of the present invention, the coculture medium is free from any auxin member other than 3,6-dichloro-o-anisic acid.

Moreover, in a preferred embodiment of the present invention, the selective drug is an antibiotic or a herbicide.

In a preferred embodiment of the present invention, the method further comprises a step for immersing the regenerated whole plant in a selective drug solution.

In another preferred embodiment of the present invention, the plant tissue is derived from a monocotyledonous plant tissue.

Further, in a preferred embodiment of the present invention, the plant tissue has been thermally-treated and/or centrifuged.

Moreover, in a preferred embodiment of the present invention, the coculture medium further comprises silver nitrate and/or copper sulfate.

The constitution of the present invention will be described in more detail below.

The present invention provides a method for producing a transformed plant, which comprises (i) a coculture step for culturing an *Agrobacterium*-inoculated plant tissue with a coculture medium containing 3,6-dichloro-o-anisic acid, 4-amino-3,5,6-trichloropicolinic acid and/or 2,4,5-trichlorophenoxyacetic acid, and (ii) a regeneration step for culturing the tissue obtained in (i) with a regeneration medium containing a selective drug to thereby induce regeneration, wherein said method does not comprise, between the coculture step and the regeneration step, any selection step for culturing the cocultured tissue with an auxin-containing medium to select a transformant by drug selection.

*Agrobacterium*-mediated transformation of a plant tissue is generally accomplished by the following steps: (i) an inoculation step for inoculating *Agrobacterium* into the plant tissue; (ii) a coculture step for culturing the plant tissue with a coculture medium containing 2,4-dichlorophenoxyacetic acid (2,4-D); (iii) a selection step for culturing the plant tissue with a selective medium containing 2,4-D and a selective drug; and (iv) a regeneration step for culturing the plant tissue with a regeneration medium containing a selective drug.

In conventional transformation methods as shown above, 2,4-D is often used as an auxin member in the coculture step, and little attempt has been made to use another auxin member in place of 2,4-D or in combination with 2,4-D in a coculture medium. In the present invention, the terms "auxin" and "auxin member" are intended to include both naturally occurring auxin and artificially synthesized auxin, which are known in the art. Examples include 2,4-dichlorophenoxyacetic acid (2,4-D), 3,6-dichloro-o-anisic acid (dicamba), 4-amino-3,5,6-trichloropicolinic acid (picloram), 2,3,5-triiodobenzoic acid (TIBA), 2,4,5-trichlorophenoxyacetic acid (2,4,5-T), indoleacetic acid (IAA), indolebutyric acid (IBA) and naphthaleneacetic acid (NAA), etc.

Moreover, in conventional *Agrobacterium*-mediated transformation methods using a coculture medium containing 2,4-D as the only auxin member, the coculture step must be followed by a selection step for selecting a transformant based on the presence or absence of gene transfer. In the conventional methods, it was difficult to obtain a plant tissue whose post-transformational regeneration rate and vigor were sufficient to obtain a transformed whole plant, unless this selection step was performed. In the present invention, a coculture medium is prepared to contain dicamba, picloram and/or 2,4,5-T, preferably dicamba alone, as an auxin member for use in the coculture step. When using a coculture medium of such composition, it is possible to obtain a plant tissue whose post-transformational regeneration rate and vigor are sufficient to obtain a transformed whole plant, even if the selection step is eliminated and the regeneration step is performed directly.

To determine whether a plant has been transformed or not, various known techniques may be used. For example, when a reporter gene (e.g., GUS (β-glucuronidase) gene, luciferase gene or GFP gene) is used as a gene to be transformed, the expression sites of these reporter genes may be visually confirmed for the presence or absence of transformation in a simple known manner. Alternatively, when using a selection marker gene such as an antibiotic resistance gene or a herbicide resistance gene, the development of resistance to the marker can be used as an indicator to confirm the presence or absence of transformation by culturing plant cells in a medium containing the antibiotic or herbicide or by treating a plant with a solution of the antibiotic or herbicide.

More accurate determination of whether a plant has been transformed or not may be accomplished, for example, by Southern hybridization technique for confirming integration of a transgene into the plant chromosome, and confirmation of transgene expression in progeny plants (inheritance to the progeny). Southern hybridization may be performed in a widely known manner, for example, as described in Molecular Cloning (Non-patent Publication No. 29). Likewise, the confirmation of transgene expression in progeny plants may be accomplished by any technique used for examining the expression of a reporter gene (e.g., GUS gene) or a selection marker gene (e.g., herbicide resistance gene), more specifically but not limited to, the technique described in Non-patent Publication No. 11.

Explanation will be given below for each step in the method of the present invention for increasing transformation efficiency in plants.

(1) *Agrobacterium* Inoculation Step

The plant tissue used in the present invention is inoculated with *Agrobacterium*. The term "inoculation" or "inoculated" used herein is intended to mean that *Agrobacterium* is contacted with a plant tissue, and various techniques for *Agrobacterium* inoculation are known in the art. Examples of such techniques include those in which a plant tissue is added to a suspension of *Agrobacterium* suspended in a liquid medium, those in which an *Agrobacterium* suspension is directly added dropwise to a plant tissue on a coculture medium, those in which an *Agrobacterium* suspension is injected into a plant tissue, and those in which a plant tissue is immersed in an *Agrobacterium* suspension and incubated under reduced pressure. However, the *Agrobacterium*-inoculated plant tissue used in the present invention is not limited to those inoculated with *Agrobacterium* by these techniques.

In this *Agrobacterium* inoculation step, to improve the *Agrobacterium*-mediated transformation efficiency, for example, various additives (e.g., acetosyringone, surfactants, porous ceramics) may be incorporated into an *Agrobacterium* suspension.

*Agrobacterium* that can be used in the present invention may be any known *Agrobacterium*. In a preferred embodiment of the present invention, examples of *Agrobacterium* include, but are not limited to, LBA4404, EHA101 and AGL1, C58C1 and others. In a case where the vector used is not a super-binary vector (Non-patent Publications No. 10 and 11), it is preferable to use a strain carrying Ti plasmid pTiBo542 from *Agrobacterium* A281 (Non-patent Publication No. 31) in terms of transformation efficiency.

*Agrobacterium* is known to have the property of introducing a gene into the plant genome, wherein the gene has been inserted into T-DNA within a plasmid in the *Agrobacterium*. For this reason, *Agrobacterium* that can be used in the present invention has a plasmid in which a gene to be expressed is inserted into the T-DNA. Then, *Agrobacterium* having this plasmid may be inoculated into a plant tissue to achieve plant transformation, so that a preferred character is imparted to plant cells in the tissue. Examples of a plasmid for *Agrobacterium* that can be used in the present invention include, but are not limited to, pSB131, U0009B, U0017S, pSB134, pNB131 and pIG121Hm and others. In a case where the *Agrobacterium* strain used does not carry Ti plasmid pTiBo542, it is preferable to use a super-binary vector (Non-patent Publications No. 10 and 11) in terms of transformation efficiency.

The source plant of the plant tissue that can be used in the present invention may be either a monocotyledon or a dicotyledon, preferably a monocotyledon, more preferably maize, wheat or barley, and most preferably maize. Moreover, the plant tissue that can be used in the present invention may be, for example, a plant cell, a leaf, a root, a stem, a fruit, an immature embryo, a callus, a flower bud, a germination site in a mature seed, or a plant tissue of any other sites, preferably an immature embryo, a flower bud or a germination site in a mature seed, and most preferably an immature embryo. As used herein, the term "immature embryo" is intended to mean the embryo of an immature seed under maturation after pollination. The stage (maturation phase) of the immature embryo used in the method of the present invention is not limited in any way, and it may be collected at any stage after pollination. It is most preferably at a post-pollination stage of 7 to 14 days.

To increase the transformation efficiency, such plant tissues as shown above may also be subjected to various treatments. Examples of such treatments include thermal treatment (Patent Publication No. 1), centrifugation (Patent Publication No. 2), thermal treatment and centrifugation (Patent Publication No. 4), as well as pressurization (Patent Publication No. 5).

(2) Coculture Step

In this step, plant cells inoculated with *Agrobacterium* as described above are cultured together with the *Agrobacterium* with a medium containing an auxin member to thereby ensure DNA introduction from the *Agrobacterium* into the plant cells. The medium used in this step is referred to herein as "coculture medium." The coculture medium may be any medium commonly used for plant cell culture, including those based on LS inorganic salts (Non-patent Publication No. 32) or N6 inorganic salts (Non-patent Publication No. 33), more specifically LS-AS medium.

According to conventional transformation methods, such a coculture medium contains 2,4-dichlorophenoxyacetic acid (2,4-D) as an auxin member. In the present invention, one of the features is to comprise 3,6-dichloro-o-anisic acid (dicamba), 4-amino-3,5,6-trichloropicolinic acid (picloram) and/or 2,4,5-trichlorophenoxyacetic acid (2,4,5-T) in the coculture medium. In a preferred embodiment of the present invention, the coculture medium is free from any auxin member other than dicamba, picloram and 2,4,5-T. In a more preferred embodiment of the present invention, the coculture medium is free from any auxin member other than dicamba.

The total amount of dicamba, picloram and/or 2,4,5-T in the coculture medium may be the same as that of 2,4-D in conventional methods, preferably 0.5 to 3.0 mg/l, more preferably 0.5 to 2.5 mg/l, even more preferably 1.0 to 2.0 mg/l, and most preferably 1.5 mg/l.

To increase the transformation efficiency, the coculture medium may further comprise various additives, in addition to dicamba, picloram and/or 2,4,5-T. Examples of such additives include silver nitrate (Patent Publication No. 3), copper sulfate (Non-patent Publication No. 6), and cysteine (Non-patent Publication No. 21).

In this step, the coculture medium comprises dicamba, picloram and/or 2,4,5-T as the only auxin member or comprises dicamba, picloram and/or 2,4,5-T and other auxin member(s). Since auxin members generally have the ability to induce dedifferentiation in plant tissues, almost every plant tissue is partially or fully turned into a dedifferentiated tissue (callus) during this step. The term "dedifferentiated tissue" or "callus" used herein is intended to mean a tissue obtained by culturing a part (explant) of a differentiated plant tissue with a medium containing a plant growth regulator such as auxin and cytokinin, wherein such a tissue is defined as an amorphous cell aggregate in an undifferentiated state which has lost the original form as a plant tissue.

Thus, all embodiments involving such a dedifferentiated tissue fall within the scope of the present invention, including those where the coculture step is started with a dedifferentiated tissue, and those where a differentiated plant tissue fully or partially dedifferentiates during the coculture step.

The term "culture" in this step is intended to mean that a plant tissue is placed on a solidified coculture medium or in a liquid coculture medium and is allowed to grow at an appropriate temperature under appropriate light/dark conditions for an appropriate period. The coculture medium may be solidified by addition of any solidifying agent known in the art, including agarose. The culture temperature in this step may be selected as appropriate, and is preferably 20° C. to 35° C., more preferably 25° C. Moreover, culture in this step is preferably accomplished in the dark, but is not limited thereto. The culture period in this step may also be selected as appropriate, and is preferably 1 to 10 days, more preferably 7 days.

(3) Selection Step

In conventional *Agrobacterium*-mediated plant transformation methods, this step is an essential step. However, in the present invention, one of the features is to note this step and move directly to the subsequent regeneration step. Thus, in the present invention, this step is not necessary. However, a brief explanation will be given below on the selection step in the conventional methods so as to clarify differences between the present invention and the conventional methods.

In this step, the plant tissue after the above coculture step is cultured with a medium containing an auxin member to select a transformant based on the presence or absence of gene transfer. The medium used in this step is referred to herein as "selective medium" and contains a selective drug or the like for selection based on the presence or absence of gene transfer.

This step is repeated for several rounds in the conventional methods while varying the composition of medium components. For example, in the selection step repeated for several rounds, the selective drug concentration may be elevated at each round to ensure a higher reliability of drug selection, so that the possibility of obtaining a transformed whole plant can be increased. This selection step is preferably repeated for at least 2 rounds, more preferably 3 rounds. When repeated for several rounds, this step requires a period of about 10 days to 3 weeks for each round, and the total period required for several rounds of selection is about 5 to 10 weeks. Thus, this step is the most time-consuming step in *Agrobacterium*-mediated plant transformation.

(4) Regeneration Step

As described above, the present invention is characterized by using a coculture medium of specific composition in the coculture step and by eliminating the selection step which has hitherto been deemed essential. Thus, the regeneration step in the present invention is accomplished in the same manner as commonly used for *Agrobacterium*-mediated plant transformation. The regeneration step described below is the same as that used in the conventional methods. The following description is provided for illustrative purposes and is not intended to limit the present invention.

In the conventional methods, this step is one in which the tissue selected in the selection step is allowed to regenerate by being cultured with a regeneration medium. In the present invention, this step is one in which the tissue after the above coculture step is allowed to regenerate by being cultured with a regeneration medium. Thus, this step is an essential step both in the conventional methods and in the present invention. The medium used in this step is referred to herein as "regeneration medium." The regeneration medium contains no auxin member, but contains a selective drug. Examples of a medium that can be used as a regeneration medium include those based on LS inorganic salts or N6 inorganic salts, more specifically LSZ medium.

Also in the present invention, the regeneration medium contains a selective drug. To select a transformed plant, the plant tissue after the coculture step may be cultured with the regeneration medium containing a selective drug and then tested for the presence or absence of resistance to the selective drug. The selective drug that can be used in the present invention may be any drug commonly used in the art. For example, it is possible to use an antibiotic and/or a herbicide as a selective drug. Examples of an antibiotic available for use include hygromycin, kanamycin or blasticidin S. Likewise, examples of a herbicide available for use include phosphinothricin, bialaphos or glyphosate.

For this step, DNA inserted into T-DNA in Agrobacterium needs to comprise not only a gene to be expressed in a plant, but also a resistance gene for a selective drug. Such a resistance gene for a selective drug is known in the art. In this step, for example, when a regeneration medium containing hygromycin as a selective drug is used for regeneration, the hygromycin resistance gene should be introduced from Agrobacterium into the plant.

Alternatively, a transformed plant may also be selected based on the sugar requirement of plant cells. Sugars assimilable by plant cells include sucrose, glucose and so on, but it is known that mannose cannot be assimilated. Thus, when cultured with a medium containing mannose as the only carbon source, plant tissues will die because there is no assimilable sugar. Selection based on sugar requirement relies on this principle. Namely, for use in this selection method, DNA inserted into T-DNA in Agrobacterium needs to comprise not only a gene to be expressed by a plant, but also a gene for phosphomannose isomerase (PMI). In this case, plant cells introduced with the PMI gene acquire the ability to assimilate mannose as a carbon source. Thus, only plant tissues transformed with such Agrobacterium as shown above can grow with a medium containing mannose as the only carbon source, whereby only transformed plant tissues can be selected (Non-patent Publication No. 16). Such a method is also possible for other sugars. For example, plant cells introduced with the xylose isomerase gene acquire the ability to assimilate xylose as a carbon source, and hence are applicable to such a method.

Thus, when a transformed plant is selected based on sugar requirement, a gene enabling the assimilation of sugars that are generally not assimilable by plant cells should be introduced from Agrobacterium into the plant tissue. Such a gene is known in the art and, for example, the PMI gene, the xylose isomerase gene or the like may be used for this purpose. Moreover, the regeneration medium should be prepared to exclude sucrose, glucose and other sugars, which are generally assimilable by plant cells and are generally contained in a medium. In place of these sugars, the regeneration medium contains only sugars which are not assimilable as carbon sources by normal plant cells. In this case, "sugars which are not assimilable by normal plant cells" are intended to mean sugars that cannot be used as nutrient sources because wild-type plant cells have no genes encoding metabolic enzymes for these sugars. Examples include mannose, xylose, etc.

Alternatively, an easily detectable gene may be introduced as a screening indicator to select a transformed plant based on the presence or absence of expression of this gene. Examples of such a gene serving as a screening indicator include the GFP gene, etc. Techniques to detect cells or tissues expressing these genes are known in the art. Selection may also be accomplished, e.g., by monitoring the expression site of such a gene as shown above and distinguishing this expression site.

The term "regeneration" used herein is intended to mean that a fully or partially dedifferentiated plant tissue acquires again the properties of the original plant tissue or whole plant. In the present invention, dedifferentiation occurs in all or a part of almost every Agrobacterium-inoculated plant tissue by the action of auxin member(s) in the coculture medium. Thus, when subjected to the regeneration step, a dedifferentiated tissue will be able to regenerate, whereby a perfect transformed whole plant can be obtained. Determination of whether regeneration has occurred or not may be readily accomplished by observation of plant morphology, for example, by determining whether a specific differentiated plant organ (e.g., stem, leaf) develops from a dedifferentiated tissue.

As used herein, the term "vigor" is intended to mean the growth vigor of a regenerated plant. The vigor of a plant may be measured by any known technique used in the art. For example, in the case of maize, scoring may be performed as follows for each transformed plant tissue after the regeneration step: transformed plant tissue showing no regeneration=0, transformed plant tissue giving a regenerated shoot whose maximum length is less than 5 mm=1, transformed plant tissue giving a regenerated shoot whose maximum length is 5 mm to less than 2 cm=2, and transformed plant tissue giving a regenerated shoot whose maximum length is 2 cm or longer=3, followed by calculating a mean value for all transformed plant tissues to thereby determine their vigor. The method of evaluation of vigor is not limited to this technique, and appropriate modifications may be made to well-known techniques, e.g., depending on the type of target to be evaluated.

The term "culture" in this step is intended to mean that a plant tissue is placed on a solidified regeneration medium or in a liquid regeneration medium and is allowed to grow at an appropriate temperature under appropriate light/dark conditions for an appropriate period. The regeneration medium may be solidified, for example, with agar or the like as shown above. The culture temperature in this step may be selected as appropriate, and is preferably 20° C. to 35° C., more preferably 25° C. Moreover, culture in this step is preferably accomplished in the light for 16 to 24 hours a day, but is not limited thereto. The culture period in this step may also be selected as appropriate, and is preferably 7 to 21 days, more preferably 14 days.

If desired, following this step, the resulting regenerated whole plant may be immersed in a selective drug solution before being provided for a next step, whereby the possibility of obtaining a transformed whole plant can further be increased. To prevent the whole plant from repelling the selective drug siltation, the regenerated whole plant may be treated, for example, under reduced pressure and/or with a surfactant during immersion in the selective drug solution.

After this step, a perfect transformed whole plant can be easily obtained in a manner known in the art.

Advantages of the Invention

The present invention enables the elimination of the selection step subsequent to the coculture step during Agrobacterium-mediated plant transformation. As shown in FIG. 3, in a case where a coculture medium is prepared to contain 2,4-D alone as an auxin member and the selection step is eliminated, the regeneration rate is as low as 15.8% and the regenerated plants have a vigor as low as 0.3. At such a low regeneration rate and vigor, it is very difficult to obtain a transformed whole plant. In contrast, in a case where a coculture medium is prepared to contain dicamba alone as an auxin member and the selection step is eliminated, the regeneration rate is as high as 97.4% and the regenerated plants have a vigor as high as 2.3, thus indicating that it is possible to obtain a transformed whole plant at a practically sufficient level, even when the selection step is eliminated.

In conventional cases, the selection step is repeated for several rounds, commonly for 3 rounds, and each round requires a period of about 10 days to 3 weeks. Thus, the present invention enables the production of a transformed whole plant within a significantly shorter period of time than in conventional methods.

Plasmid name: U0009B.prj

Plasmid size: 12347 bp

Figure 3:
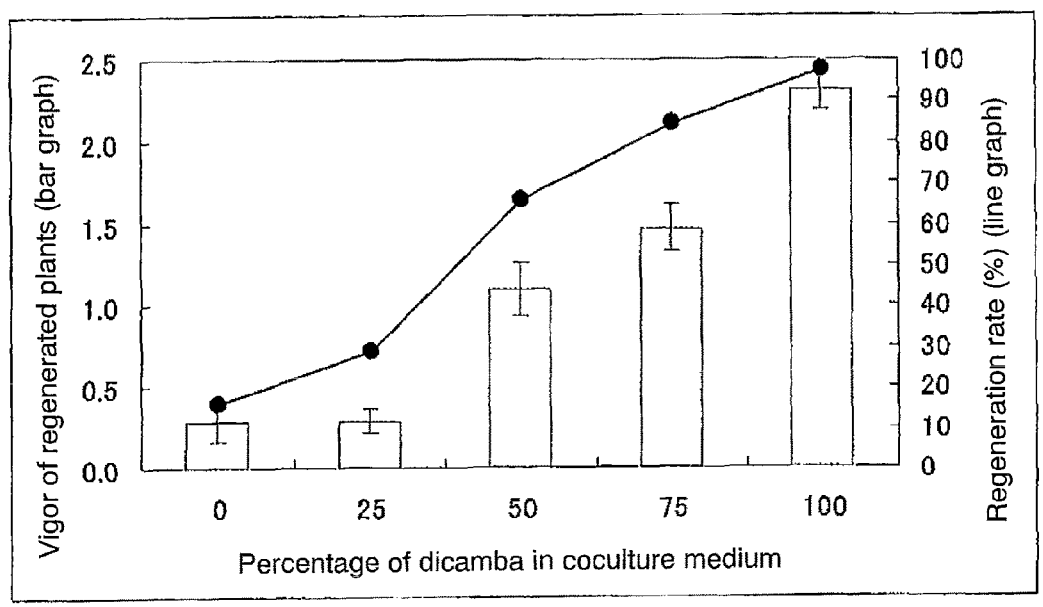

FIG. 3 is a graph showing the effects of the dicamba/2,4-D ratio on the plant regeneration rate from cocultured immature embryos and on the vigor of regenerated plants. 38 immature embryos were provided for each test. The bar graph (vertical axis on the left side) represents the vigor of regenerated plants, the line graph (vertical axis on the right side) represents the regeneration rate (calculated by dividing the number of immature embryos showing regeneration in each test by the number of inoculated immature embryos), and the horizontal axis represents the percentage of dicamba contained in a coculture medium. The numerical values on the horizontal axis mean that auxin is contained in the coculture medium at the following ratios: 0 mg/l dicamba+1.5 mg/l 2,4-D (0% dicamba), 0.375 mg/l dicamba+1.125 mg/l 2,4-D (25% dicamba), 0.75 mg/l dicamba+0.75 mg/l 2,4-D (50% dicamba), 1.125 mg/l dicamba+0.375 mg/l 2,4-D (75% dicamba), and 1.5 mg/l dicamba+0 mg/l 2,4-D (100% dicamba). The vigor of regenerated plants was evaluated by scoring as follows: immature embryo showing no regeneration=0, immature embryo giving a regenerated shoot whose maximum length is less than 5 mm=1, immature embryo giving a regenerated shoot whose maximum length is 5 mm to less than 2 cm=2, and immature embryo giving a regenerated shoot whose maximum length is 2 cm or longer=3.

Figure 4:
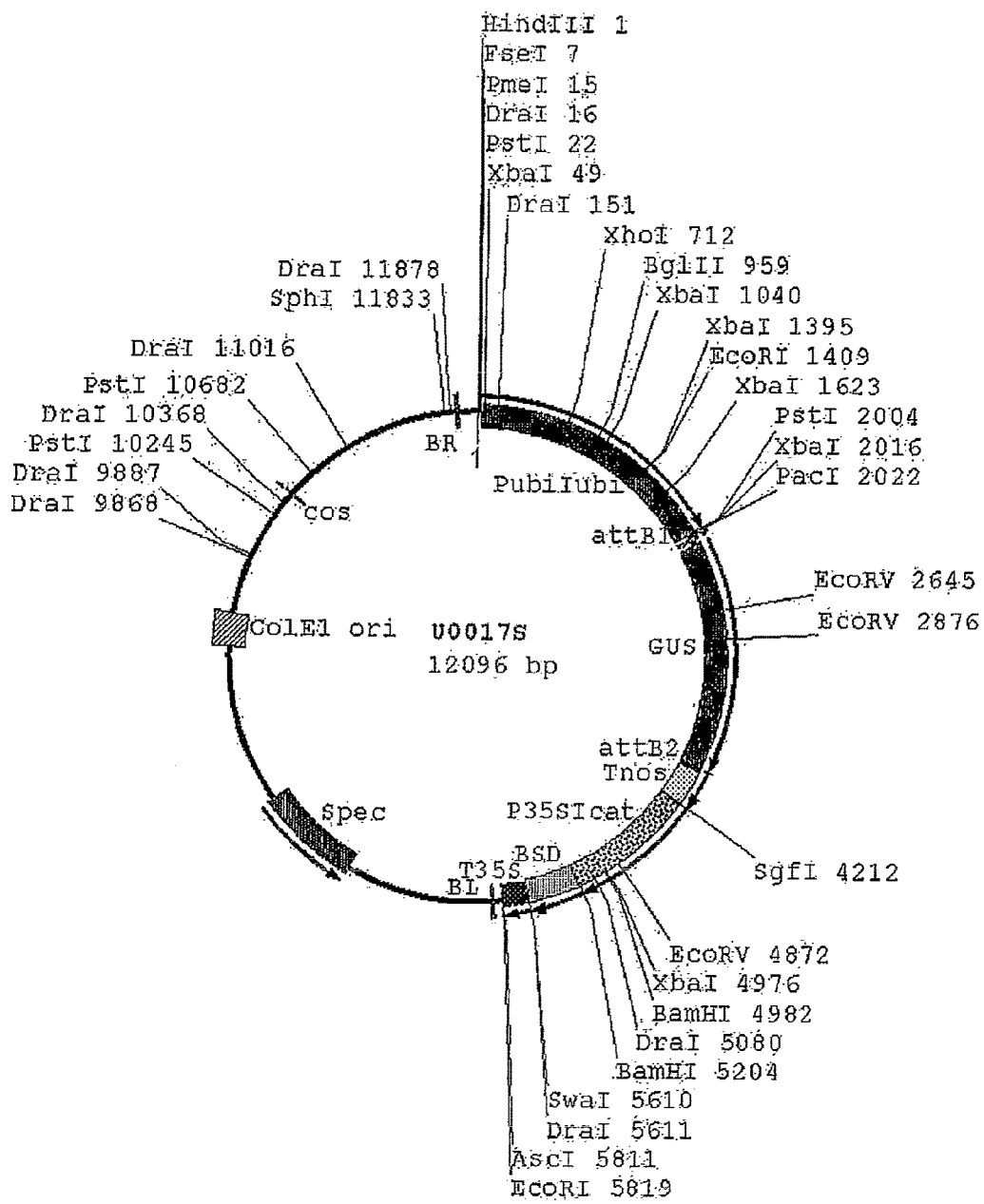

FIG. 4 shows the structure of plasmid U0017S from *Agrobacterium* strain LBA4404 (U0017S).

Plasmid name; 3428.prj

Plasmid size: 12096 bp

EXAMPLES

The present invention will now be further described by way of the following examples, which are provided for illustrative purposes only and are not intended to limit the present invention. The scope of the present invention is determined on the basis of the claims. Further, based on the detailed description, modifications and changes will be apparent to those skilled in the art.

Example 1

Regeneration of whole plants from immature embryos cultured on coculture medium supplemented with various types of auxin Material and Method Maize (variety: A188) immature embryos (1.0 to 1.5 mm in size) at 7 to 14 days after pollination were aseptically collected and washed once with LS-inf liquid medium (Non-patent Publication No. 11), followed by pretreatment (thermal treatment at 46° C. for 3 minutes and centrifugation at 15,000 rpm for 10 minutes) to increase gene transfer efficiency. In LS-inf liquid medium containing 100 µM acetosyringone, *Agrobacterium* strain LBA4404 (pSB134) (Non-patent Publication No. 27) was suspended at about $1.0 \times 10^9$ cfu/ml to prepare an inoculum. The thermally-treated and centrifuged immature embryos were mixed with the inoculum, vortexed for 30 seconds, and then allowed to stand for 5 minutes at room temperature. The *Agrobacterium*-inoculated immature embryos were placed, with their embryonic discs facing up, onto a coculture medium containing 2,4,5-T (2,4,5-trichlorophenoxyacetic acid), picloram (4-amino-3,5,6-trichloropicolinic acid), TIBA (2,3,5-triiodobenzoic acid) or dicamba (3,6-dichloro-o-anisic acid) at a concentration of 1.5 mg/l in LS-AS medium (Non-patent Publication No. 11; solidified with 8 g/l agarose) which had been prepared to exclude 2,4-D (2,4-dichlorophenoxyacetic acid) and contain 5 µM $AgNO_3$ and 5 µM $CuSO_4$. A control medium was prepared to contain 5 µM $AgNO_3$ and 5 µM $CuSO_4$ in LS-AS medium (solidified with 8 g/l agarose).

The immature embryos cultured in the dark at 25° C. for 7 days were placed onto LSZ medium (Non-patent Publication No. 11) containing 10 µM $CuSO_4$ and 30 mg/l hygromycin, and then cultured in the light at 25° C. for about 2 weeks. The number of immature embryos which regenerated into whole plants was determined, and the regenerated plants were examined for their vigor.

Results

Figure 1:
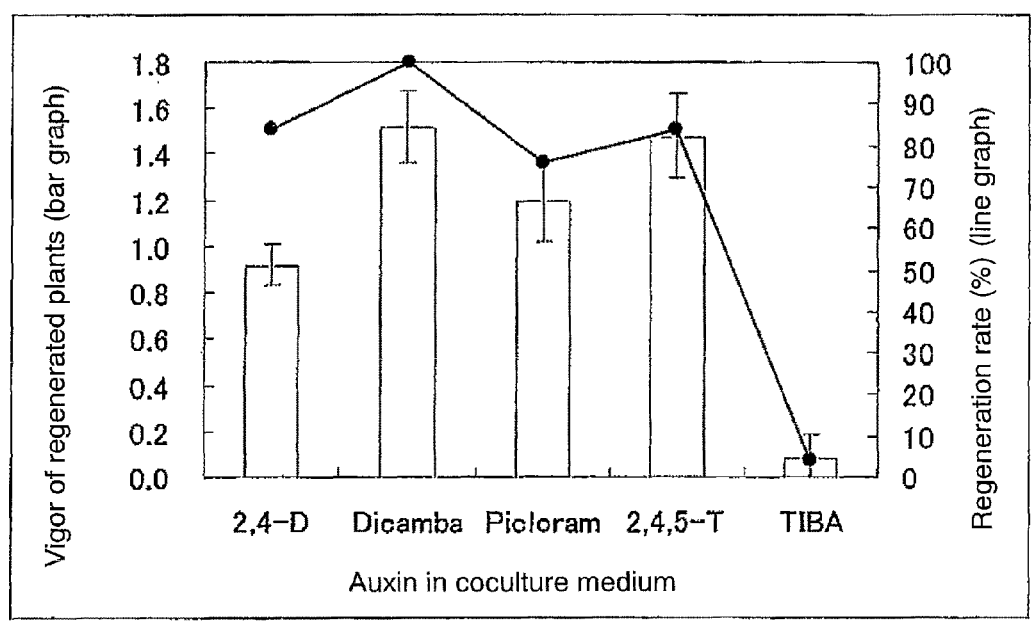
FIG. 1 is a graph showing the effects of auxin type on the plant regeneration rate from cocultured immature embryos and on the vigor of regenerated plants. 25 immature embryos were provided for each test. The bar graph (vertical axis on the left side) represents the vigor of regenerated plants, the line graph (vertical axis on the right side) represents the regeneration rate (calculated by dividing the number of immature embryos showing regeneration in each test by the number of inoculated immature embryos), and the horizontal axis represents the type of auxin contained in a coculture medium. The auxin concentration in the coculture medium was set to 1.5 mg/l for each test. The vigor of regenerated plants was evaluated by scoring as follows: immature embryo showing no regeneration=0, immature embryo giving a regenerated shoot whose maximum length is less than 5 mm=1, immature embryo giving a regenerated shoot whose maximum length is 5 mm to less than 2 cm=2, and immature embryo giving a regenerated shoot whose maximum length is 2 cm or longer=3.

Except for the TIBA case, the immature embryos cultured on each coculture medium were found to regenerate into whole plants with an efficiency as high as 70% or more. At 2 weeks after the immature embryos were placed onto a regeneration medium, the regenerated whole plants were evaluated for their growth on a 4-point scale ranging from 0 (stop to grow) to 3 (vigorously grow). As a result, plants which regenerated from the immature embryos cultured on the coculture medium containing 2,4-D were found to grow less than plants which regenerated from the immature embryos cultured on the coculture medium containing dicamba, picloram or 2,4,5-T (FIG. 1) (Table 1).

TABLE 1

| | Regeneration rate (%) | Vigor |
|---|---|---|
| 2,4-D | 84.0 | 0.9 |
| Dicamba | 100 | 1.5 |
| Picloram | 76.4 | 1.2 |
| 2,4,5-T | 84.0 | 1.5 |
| TIBA | 4.0 | 0.1 |

Example 2

Effect of Dicamba and 2,4-D in Coculture Medium on Regeneration

Material and Method

Figure 2:
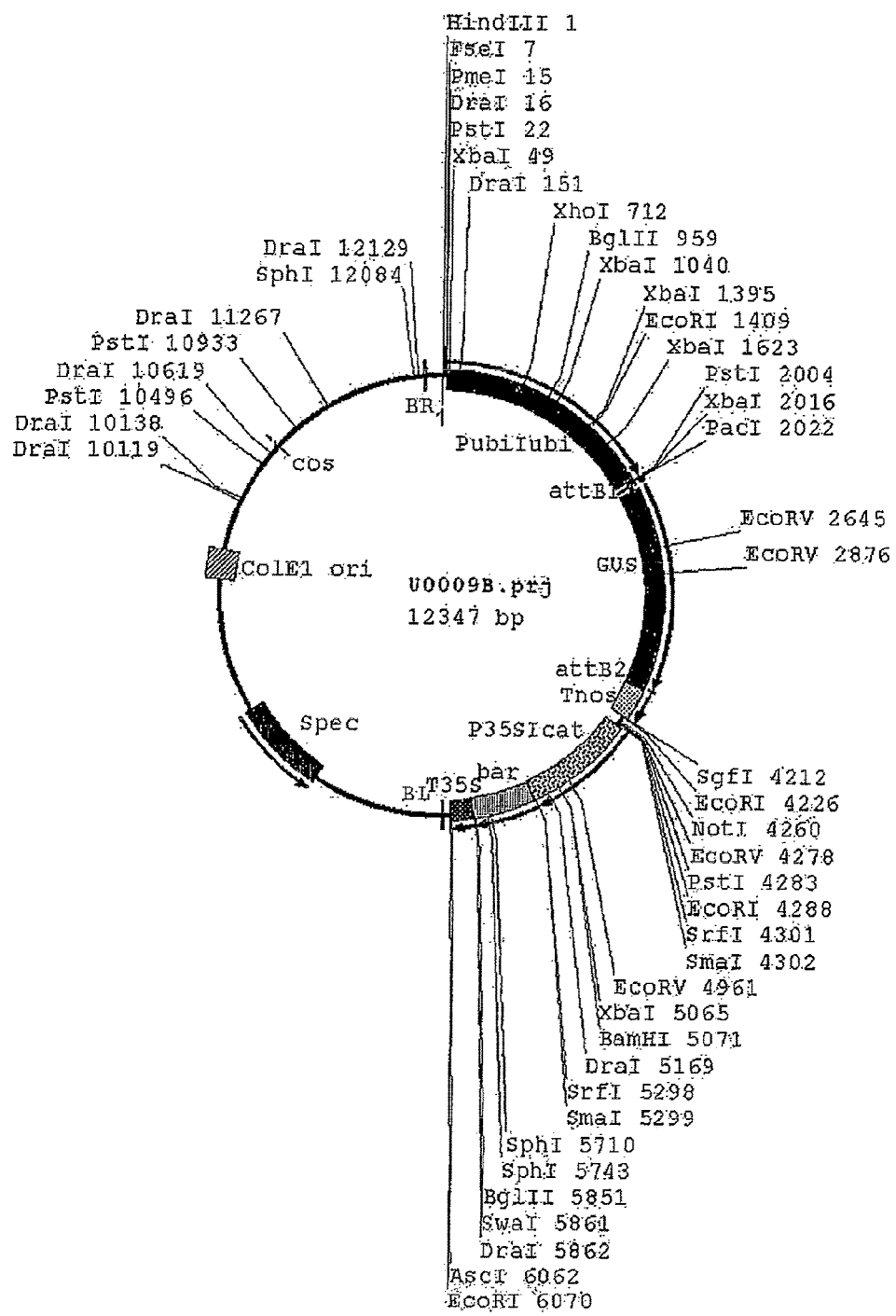
FIG. 2 shows the structure of plasmid U0009B from *Agrobacterium* strain LBA4404 (U0009B).

The vector U0009B shown in FIG. 2 and SEQ ID NO: 1 was constructed by adding necessary elements to a vector having pSB11 (Non-patent Publication No. 28) as a skeletal structure. Immature embryos (variety: A188) were inoculated with Agrobacterium strain LBA4404 (U0009B) in the same manner as shown in Example 1 and then placed onto LS-AS medium (solidified with 8 g/l agarose) containing 5 µM AgNO$_3$ and 5 µM CuSO$_4$, which had been prepared to replace auxin in the medium by 0 mg/l dicamba and 1.5 mg/l 2.4-D (0% dicamba), 0.375 mg/l dicamba and 1.125 mg/l 2,4-D (25% dicamba), 0.75 mg/l dicamba and 0.75 mg/l 2,4-D (50% dicamba), 1.125 mg/l dicamba and 0.375 mg/l 2,4-D (75% dicamba), or 1.5 mg/l dicamba and 0 mg/l 2,4-D (100% dicamba). The immature embryos cultured in the dark at 25° C. for 7 days were placed onto LSZ medium (Non-patent Publication No. 11) containing 10 µM CuSO$_4$ and 30 mg/l hygromycin, and then cultured in the light at 25° C. for about 2 weeks. The number of immature embryos which regenerated into whole plants was determined, and the regenerated plants were examined for their vigor.

Results

The immature embryos cultured on each coculture medium were found to regenerate into whole plants, and a higher percentage of dicamba in the coculture medium resulted in a higher regeneration rate and more vigorous growth of the regenerated plants (FIG. 3).

Example 3

Effect of Hygromycin Concentration in Regeneration Medium on Transformation Efficiency Material and Method Immature embryos (variety: A188) were inoculated with Agrobacterium strain LBA4404 (pSB134) in the same manner as shown in Example 1 and then placed onto a coculture medium containing dicamba at a concentration of 1.5 mg/l in LS-AS medium (Non-patent Publication No. 11; solidified with 8 g/l agarose) which had been prepared to exclude 2,4-D and contain 5 µM AgNO$_3$ and 5 µM CuSO$_4$.

After being cultured in the dark at 25° C. for 3 days, the immature embryos were placed onto LSZ medium (Non-patent Publication No. 11) containing 10 µM CuSO$_4$ and 0, 15, 30, 50 or 75 mg/l hygromycin, and then cultured in the light at 25° C. for about 2 weeks. The number of immature embryos which regenerated into whole plants was determined, and the regenerated plants were examined for GUS gene expression.

Results

In the hygromycin-free regeneration medium, all the placed immature embryos were found to regenerate into whole plants. However, almost all of them failed to show GUS gene expression, and even among whole plants showing GUS gene expression, all showed a dotted or striped pattern of expression. There was no whole plant showing uniform GUS expression throughout leaves. Similar results were also observed in the plants which regenerated on the regeneration medium containing 15 mg/l hygromycin. In the immature embryos placed on the regeneration media containing 30 mg/l or more hygromycin, their regeneration rate was lower than that in the medium containing 15 mg/l hygromycin or free from hygromycin. However, most of the regenerated plants showed GUS gene expression, and cases showing uniform expression throughout leaves were also observed in 9.1% to 19.0% of the inoculated immature embryos. Moreover, among the plants which regenerated on the media containing 30 mg/l or more hygromycin, some had leaves with a striped pattern of green and white. When analyzed by GUS assay, these plants showed GUS gene expression only in green segments (Table 2).

TABLE 2

Effect of hygromycin concentration in regeneration medium on transformation efficiency

| Test No. | Hm conc. (mg/l) | Number of immature embryos | | | | Striped, dotted (C) | C/A (%) | GUS− |
|---|---|---|---|---|---|---|---|---|
| | | Inoculated (A) | Regenerated | GUS+ (B) | B/A (%) | | | |
| 1 | 0 | 21 | 21 | 0 | 0 | 2 | 9.5 | 19 |
| | 15 | 22 | 21 | 0 | 0 | 3 | 14.3 | 18 |
| | 30 | 21 | 15 | 2 | 9.5 | 8 | 38.1 | 5 |
| | 50 | 22 | 15 | 2 | 9.1 | 8 | 36.4 | 5 |
| | 75 | 21 | 15 | 4 | 19.0 | 7 | 33.3 | 4 |
| 2 | 0 | 20 | 20 | 0 | 0 | 9 | 45.0 | 11 |
| | 15 | 17 | 17 | 0 | 0 | 7 | 41.1 | 10 |
| | 30 | 17 | 14 | 3 | 17.6 | 10 | 58.8 | 1 |
| | 50 | 17 | 3 | 2 | 11.7 | 0 | 0 | 1 |
| | 75 | 16 | 6 | 2 | 12.5 | 4 | 25.0 | 0 |

Example 4

Transformation using Blasticidin S Deaminase Gene as a Selection Marker

Material and Method

Necessary elements were added to a vector having pSB11 as a skeletal structure to construct vector U0017S shown in FIG. 4 and SEQ ID NO: 2. Immature embryos (variety: A188) were inoculated with *Agrobacterium* strain LBA4404 (U0017S) in the same manner as shown in Example 1 and then placed onto a coculture medium containing dicamba at a concentration of 1.5 mg/l in LS-AS medium (Non-patent Publication No. 11; solidified with 8 g/l agarose) which had been prepared to exclude 2,4-D and contain 5 µM AgNO$_3$ and 5 µM CuSO$_4$.

After being cultured in the dark at 25° C. for 3 days, the immature embryos were placed onto LSZ medium (Non-patent Publication No. 11) containing 10 µM CuSO$_4$ and 2 mg/l blasticidin S, and then cultured in the light at 25° C. for about 2 weeks. The number of immature embryos which regenerated into whole plants was determined, and the regenerated plants were examined for GUS gene expression.

Results

Almost all of the inoculated immature embryos were found to regenerate into whole plants. Leaves of these plants were partially excised and analyzed by GUS assay, indicating that 19 plants, which constitute 41.3% of the inoculated immature embryos, showed GUS gene expression throughout their leaves. On the other hand, 14 plants showed a dotted or striped pattern of expression, and 12 plants were GUS-negative. These results indicate that when the blasticidin S deaminase gene is used as a selection marker, it is also possible to obtain transformed plants with high efficiency within a short period of time (Table 3).

TABLE 3

Transformation efficiency measured when immature embryos immediately after coculture are cultured on regeneration medium containing blasticidin (BS)

| Number of immature embryos | | | B/A | Striped, | C/A | |
|---|---|---|---|---|---|---|
| Inoculated (A) | Regenerated | GUS+ (B) | (%) | dotted (C) | (%) | GUS– |
| 46 | 45 | 19 | 41.3 | 14 | 3.04 | 12 |

Example 5

Effect of Selective Pressure Treatment Before Placing on Rooting Medium

Material and Method

Immature embryos (variety: A188) were inoculated with *Agrobacterium* strain LBA4404 (U0009B) in the same manner as shown in Example 1 and then placed onto a coculture medium containing dicamba at a concentration of 1.5 mg/l in LS-AS medium (Non-patent Publication No. 11; solidified with 8 g/l agarose) which had been prepared to exclude 2,4-D and contain 5 µM AgNO$_3$ and 5 µM CuSO$_4$. After being cultured in the dark at 25° C. for 3 days, the immature embryos were placed onto LSZ medium (Non-patent Publication No. 11) containing 10 µM CuSO$_4$ and 5 mg/l PPT, and then cultured in the light at 25° C. for about 2 weeks. The immature embryos which regenerated into whole plants were immersed in a 0.3% Basta solution and incubated under reduced pressure. After return to normal pressure, the plants were placed on a rooting medium and cultured in the light at 25° C. The growth of whole plants was examined at 12 days after placing on the rooting medium, and the regenerated plants were examined for GUS expression at 21 days after placing on the rooting medium.

Results

Among the tested 78 samples, 25 samples did not grow (i.e., remained in a placed state) or died. The rest grown samples were divided into 3 ranks, based on the growth state of their shoot and the presence or absence of rooting. Among plants whose shoot was determined to be well grown, almost all of them showed GUS gene expression, regardless of the presence or absence of rooting. Likewise, among plants showing a delay in their shoot growth and no rooting, more than half of them also showed GUS gene expression. These results indicate that efficient selection of transformed plants, except for escapes, is possible for transformants obtained by using the bar gene as a selection marker, when these transformants are treated, after regeneration, with a solution of the herbicide Basta containing PPT (serving as selective pressure) as a major component (Table 4).

TABLE 4

Growth state and GUS gene expression in regenerated plants immersed in 0.3% Basta solution before placing on rooting medium

| Rank | Vigor after Basta treatment Growth state | Number of Samples | GUS+ (B) | B/A (%) | Striped, dotted (C) | C/A (%) | GUS− |
|---|---|---|---|---|---|---|---|
| A | Shoot++, root+ | 21 | 9 | 42.9 | 10 | 47.6 | 2 |
| B | Shoot++, root− | 10 | 4 | 40.0 | 4 | 40.0 | 2 |
| C | Shoot+, root− | 22 | 9 | 40.9 | 6 | 27.3 | 7 |
| Total | | 53 | 22 | 41.5 | 20 | 37.7 | 11 |
| D | Shoot± or died | 25 | 0 | 0 | 0 | 0 | 25 |

Example 6

GUS Expression in Leaves at Different Positions in Plants Expressing GUS Gene in a Dotted or Striped Pattern Material and Method The transformed plants showing GUS gene expression obtained in Example 4 were cultivated in a greenhouse. Leaves at each position were partially excised from the plants at flowering stage and analyzed by GUS assay.

Results

In the case of the plants found to show uniform GUS gene expression throughout their leaves when analyzed by GUS assay immediately after regeneration, they also showed uniform and strong GUS gene expression in their leaves at each position. In contrast, in the case of the plants showing a striped or dotted pattern of expression, their leaves at each position also showed a striped or dotted pattern of expression (Table 5).

TABLE 5

GUS expression in leaves at different positions in cultivated plants

| Plant No. | Leaf (position from the top) | | | | | | | | | | |
|---|---|---|---|---|---|---|---|---|---|---|---|
| | 1 | 2 | 3 | 4 | 5 | 6 | 7 | 8 | 9 | 10 | 11 |
| 351 | S | S | S | S | S | S | S | S | S | | |
| 352 | + | + | + | + | + | + | + | + | + | + | + |
| 353 | + | + | + | + | + | + | + | + | + | + | + |
| 354 | + | + | + | + | + | + | + | + | | | |
| 355 | + | + | + | + | + | + | + | + | + | | |
| 356 | S | S | S | S | S | S | S | S | S | S | |
| 357 | + | + | + | + | + | + | + | + | + | + | |
| 358 | + | + | + | + | + | + | + | + | + | | |
| 361 | D | D | D | D | D | D | | | | | |
| 362 | S | + | + | + | + | + | + | S | S | | |
| 363 | D | D | D | D | D | D | D | D | D | | |
| 364 | S | D | S | D | D | D | D | S | | | |
| 365 | + | + | + | + | + | + | + | | | | |
| 366 | D | D | D | D | D | S | D | S | | | |
| 367 | + | + | + | + | | | | | | | |
| 368 | + | + | + | + | + | | | | | | |
| 369 | + | + | + | + | + | + | + | + | | | |

S: striped pattern of expression,
D: dotted pattern of expression

Example 7

Transgene Expression in Progeny Plants

Material and Method

The transformed plants showing GUS gene expression obtained in Example 4 were cultivated in a greenhouse. Extracted male spikes were removed before flowering, and the floss extracted from each female spike was crossed with pollens from non-transformed A188. The resulting seeds were seeded, and leaves were partially excised from young seedlings at 7 days after seeding and analyzed by GUS assay.

Results

In the case of the plants found to show uniform GUS gene expression throughout their leaves when analyzed by GUS assay immediately after regeneration, their progeny plants separated into a group showing uniform GUS gene expression throughout leaves and a group being GUS-negative. The ratio of these groups was 1:1 in all cases, indicating that the transgene was inherited to progeny according to the Mendel's laws. Likewise, in the case of the plants showing a striped pattern of expression immediately after regeneration, their progeny plants also separated into a group showing uniform GUS gene expression throughout leaves and a group being GUS-negative, and there was no progeny plant expressing the GUS gene in a striped pattern. The GUS-positive:negative ratio was 1:1 in all cases, indicating that the transgene was also inherited to progeny according to the Mendel's laws even in the plants whose parent plants (T0) expressed the GUS gene in a striped pattern (Table 6).

TABLE 6

Expression and copy number of GUS gene in transformed plants (T0) and expression of GUS gene in progeny plants (T1)

| Transformant (T0) No. | GUS expression | Copy number of GUS gene | Number of T1 plants showing GUS expression | | Separation ratio |
|---|---|---|---|---|---|
| | | | Positive | Negative | |
| 353 | + | 1 | 19 | 14 | 1:1 |
| 354 | + | 1 | 15 | 17 | 1:1 |

TABLE 6-continued

Expression and copy number of GUS gene in transformed plants (T0) and expression of GUS gene in progeny plants (T1)

| Transformant (T0) No. | GUS expression | Copy number of GUS gene | Number of T1 plants showing GUS expression | | Separation ratio |
|---|---|---|---|---|---|
| | | | Positive | Negative | |
| 355 | + | 2 | 15 | 17 | 1:1 |
| 365 | + | 2 | 14 | 12 | 1:1 |
| 357 | + | 3 | 17 | 15 | 1:1 |
| 352 | + | 3 | 17 | 15 | 1:1 |
| 369 | + | 3 | 20 | 10 | 1:1 |
| 358 | + | 4 | 32 | 0 | |
| 356 | S | 1 | 15 | 17 | 1:1 |
| 351 | S | 2 | 16 | 16 | 1:1 |
| 362 | S | 3 | 16 | 15 | 1:1 |
| 366 | D | 2 | 22 | 7 | 3:1 |
| 363 | D | 1 | 13 | 13 | 1:1 |
| Non-transformant | — | — | 0 | 32 | — |

GUS expression
+: positive,
S: striped pattern,
D: dotted pattern

Example 8

Southern Analysis

Material and Method

According to the method of Komari et al. (Non-patent Publication No. 29), DNAs were extracted from leaves of the transformed plants showing GUS gene expression obtained in Example 4. The extracted DNAs were each treated with a restriction enzyme BamHI, and subjected to Southern analysis using the GUS gene as a probe to detect the transgene.

Southern analysis was performed as described in Molecular Cloning (Non-patent Publication No. 30).

Results

Each transformant showed a band hybridizing to the GUS probe. The band pattern differed from transformant to transformant, thus indicating that the transgene was randomly inserted onto the plant chromosome. The number of bands observed for the GUS-positive transformants was 1 to 4, and hence the copy number of the inserted transgene was found to be small in each case (Table 6).

---

The invention claimed is:

1. A method for producing a transformed maize, which comprises:
   (i) a co-culture step for culturing an *Agrobacterium*-inoculated immature maize embryo with a co-culture medium containing 3,6-dichloro-o-anisic acid, 4-amino-3,5,6-trichloropicolinic acid and/or 2,4,5-trichlorophenoxyacetic acid; said co-culture medium further comprising silver nitrate and/or copper sulfate; said co-culture medium excluding 2,4-dichloophenoxyacetic acid; wherein said *Agrobacterium* has a plasmid in which a resistance gene for a selective drug is inserted into the T-DNA; and
   (ii) a regeneration step for culturing the embryo obtained from (i) with a regeneration medium containing the selective drug to thereby induce regeneration and to produce a transformed plant,
   wherein said method does not comprise, between the co-culture step and the regeneration step, any selection step for culturing the co-cultured tissue with a medium containing an auxin and selective drug to select a transformant.

2. The method according to claim 1, wherein the co-culture medium is free from any auxin member other than 3,6-dichloro-o-anisic acid, 4-amino-3,5,6-trichloropicolinic acid and 2,4,5-trichlorophenoxyacetic acid.

3. The method according to claim 1 or 2, wherein the co-culture medium is free from any auxin member other than 3,6-dichloro-o-anisic acid.

4. The method according to claim 1, wherein the selective drug is an antibiotic, a herbicide, or a sugar that is not assimilable by wild-type plant cells.

5. The method according to claim 1, which further comprises a step for immersing the regenerated whole plant in a solution containing a selective drug.

6. The method according to claim 1, wherein the embryo has been thermally-treated and/or centrifuged.

* * * * *

SEQUENCE LISTING

<160> NUMBER OF SEQ ID NOS: 2

<210> SEQ ID NO 1
<211> LENGTH: 12347
<212> TYPE: DNA
<213> ORGANISM: Artificial
<220> FEATURE:
<223> OTHER INFORMATION: Plasmid for Agrobacterium

<400> SEQUENCE: 1

```
aagcttggcc ggccgtttaa actgcagcgt gacccggtcg tgcccctctc tagagataat      60
gagcattgca tgtctaagtt ataaaaaatt accacatatt tttttttgtca cacttgtttg     120 aagtgcagtt tatctatctt tatacatata tttaaacttt actctacgaa taatataatc     180
tatagtacta caataaatc agtgttttag agaatcatat aaatgaacag ttagacatgg      240
tctaaaggac aattgagtat tttgacaaca ggactctaca gttttatctt tttagtgtgc     300
atgtgttctc cttttttttt gcaaatagct tcacctatat aatacttcat ccattttatt     360
agtacatcca tttagggttt agggttaatg gttttttatag actaattttt ttagtacatc     420
tattttattc tattttagcc tctaaattaa gaaaactaaa actctatttt agttttttta     480
tttaataatt tagatataaa atagaataaa ataaagtgac taaaaattaa acaaataccc     540
tttaagaaat taaaaaaact aaggaaacat ttttcttgtt tcgagtagat aatgccagcc     600
tgttaaacgc cgtcgacgag tctaacggac accaaccagc gaaccagcag cgtcgcgtcg     660
```

```
ggccaagcga agcagacggc acggcatctc tgtcgctgcc tctggacccc tctcgagagt    720
tccgctccac cgttggactt gctccgctgt cggcatccag aaattgcgtg gcggagcggc    780
agacgtgagc cggcacggca ggcggcctcc tcctcctctc acggcaccgg cagctacggg    840
ggattccttt cccaccgctc cttcgctttc ccttcctcgc ccgccgtaat aaatagacac    900
cccctccaca ccctctttcc caacctcgt gttgttcgga gcgcacacac acacaaccag     960
atctccccca atccacccg tcggcacctc cgcttcaagg tacgccgctc gtcctccccc    1020
cccccccctc tctaccttct ctagatcggc gttccggtcc atggttaggg cccggtagtt   1080
ctacttctgt tcatgtttgt gttagatccg tgtttgtgtt agatccgtgc tgctagcgtt   1140
cgtacacgga tgcgacctgt acgtcagaca cgttctgatt gctaacttgc cagtgtttct   1200
ctttggggaa tcctgggatg gctctagccg ttccgcagac gggatcgatt tcatgatttt   1260
ttttgtttcg ttgcataggg tttggtttgc ccttttcctt tatttcaata tatgccgtgc   1320
acttgtttgt cgggtcatct tttcatgctt ttttttgtct tggttgtgat gatgtggtct   1380
ggttgggcgg tcgttctaga tcggagtaga attctgtttc aaactacctg gtggatttat   1440
taattttgga tctgtatgtg tgtgccatac atattcatag ttacgaattg aagatgatgg   1500
atggaaatat cgatctagga taggtataca tgttgatgcg ggttttactg atgcatatac   1560
agagatgctt tttgttcgct tggttgtgat gatgtggtgt ggttgggcgg tcgttcattc   1620
gttctagatc ggagtagaat actgtttcaa actacctggt gtatttatta attttggaac   1680
tgtatgtgtg tgtcatacat cttcatagtt acgagtttaa gatggatgga aatatcgatc   1740
taggataggt atacatgttg atgtgggttt tactgatgca tatacatgat ggcatatgca   1800
gcatctattc atatgctcta accttgagta cctatctatt ataataaaca agtatgtttt   1860
ataattattt tgatcttgat atacttggat gatggcatat gcagcagcta tatgtggatt   1920
tttttagccc tgccttcata cgctatttat ttgcttggta ctgtttcttt tgtcgatgct   1980
caccctgttg tttggtgtta cttctgcagg tcgactctag attaattaag ttatcacaag   2040
tttgtacaaa aaagcaggct catttaactt taagaaggag atatatacca tggtccgtcc   2100
tgtagaaacc ccaacccgtg aaatcaaaaa actcgacggc ctgtgggcat tcagtctgga   2160
tcgcgaaaac tgtggaattg atcagcgttg gtgggaaagc gcgttacaag aaagccgggc   2220
aattgctgtg ccaggcagtt ttaacgatca gttcgccgat gcagatattc gtaattatgc   2280
gggcaacgtc tggtatcagc gcgaagtctt tataccgaaa ggttgggcag ccagcgtat    2340 cgtgctgcgt ttcgatgcgg tcactcatta cggcaaagtg tgggtcaata tcaggaagt    2400 gatggagcat cagggcggct atacgccatt tgaagccgat gtcacgccgt atgttattgc   2460
cgggaaaagt gtacgtatca ccgtttgtgt gaacaacgaa ctgaactggc agactatccc   2520
gccgggaatg gtgattaccg acgaaaacgg caagaaaaag cagtcttact tccatgattt   2580
ctttaactat gccggaatcc atcgcagcgt aatgctctac accacgccga cacctgggt    2640 ggacgatatc accgtggtga cgcatgtcgc gcaagactgt aaccacgcgt ctgttgactg   2700
gcaggtggtg gccaatggtg atgtcagcgt tgaactgcgt gatgcggatc aacaggtggt   2760
tgcaactgga caaggcacta gcgggacttt gcaagtggtg aatccgcacc tctggcaacc   2820
gggtgaaggt tatctctatg aactgtgcgt cacagccaaa agccagacag agtgtgatat   2880
ctacccgctt cgcgtcggca tccggtcagt ggcagtgaag gcgaacagt tcctgattaa    2940 ccacaaaccg ttctacttta ctggctttgg tcgtcatgaa gatgcggact acgtggcaa    3000 aggattcgat aacgtgctga tggtgcacga ccacgcatta atggactgga ttggggccaa   3060
```

```
ctcctaccgt acctcgcatt acccttacgc tgaagagatg ctcgactggg cagatgaaca    3120
tggcatcgtg gtgattgatg aaactgctgc tgtcggcttt aacctctctt taggcattgg    3180
tttcgaagcg ggcaacaagc cgaaagaact gtacagcgaa gaggcagtca acggggaaac    3240
tcagcaagcg cacttacagg cgattaaaga gctgatagcg cgtgacaaaa accacccaag    3300
cgtggtgatg tggagtattg ccaacgaacc ggatacccgt ccgcaaggtg cacgggaata    3360
tttcgcgcca ctggcggaag caacgcgtaa actcgacccg acgcgtccga tcacctgcgt    3420
caatgtaatg ttctgcgacg ctcacaccga taccatcagc gatctctttg atgtgctgtg    3480
cctgaaccgt tattacggat ggtatgtcca aagcggcgat ttggaaacgg cagagaaggt    3540
actggaaaaa gaacttctgg cctggcagga gaaactgcat cagccgatta tcatcaccga    3600
atacggcgtg gatacgttag ccgggctgca ctcaatgtac accgacatgt ggagtgaaga    3660
gtatcagtgt gcatggctgg atatgtatca ccgcgtcttt gatcgcgtca gcgccgtcgt    3720
cggtgaacag gtatggaatt cgccgatttt tgcgacctcg caaggcatat tgcgcgttgg    3780
cggtaacaag aaagggatct tcactcgcga ccgcaaaccg aagtcggcgg cttttctgct    3840
gcaaaaacgc tggactggca tgaacttcgg tgaaaaaccg cagcagggag gcaaacaata    3900 ataccagct ttcttgtaca aagtggtgat aacagatcgt tcaaacattt ggcaataaag    3960
tttcttaaga ttgaatcctg ttgccggtct tgcgatgatt atcatataat ttctgttgaa    4020
ttacgttaag catgtaataa ttaacatgta atgcatgacg ttatttatga gatgggtttt    4080
tatgattaga gtcccgcaat tatacattta atacgcgata aaaacaaaa tatagcgcgc    4140 aaactaggat aaattatcgc gcgcggtgtc atctatgtta ctagatccga tgataagctg    4200
tcaaacatga ggcgatcgca agggcgaatt ccagcacact ggcggccgtt actagtcgag    4260
cggccgccag tgtgatggat atctgcagaa ttcgccctta gcccgggccc cgagcaataa    4320
tctccaggag atcaaatacc ttcccaagaa ggttaaagat gcagtcaaaa gattcaggac    4380
taactgcatc aagaacacag agaaagatat atttctcaag atcagaagta ctattccagt    4440
atggacgatt caaggcttgc ttcacaaacc aaggcaagta atagagattg gagtctctaa    4500
aaaggtagtt cccactgaat caaaggccat ggagtcaaag attcaaatag aggacctaac    4560
agaactcgcc gtaaagactg gcgaacagtt catacagagt ctcttacgac tcaatgacaa    4620
gaagaaaatc ttcgtcaaca tggtggagca cgacacgctt gtctactcca aaaatatcaa    4680
agatacagtc tcagaagacc aaagggcaat tgagactttt caacaaaggg taatatccgg    4740
aaacctcctc ggattccatt gcccagctat ctgtcacttt attgtgaaga tagtggaaaa    4800
ggaaggtggc tcctacaaat gccatcattg cgataaagga aaggccatcg ttgaagatgc    4860
ctctgccgac agtggtccca agatggaccc cccacccacg aggagcatcg tggaaaaaga    4920
agacgttcca accacgtctt caaagcaagt ggattgatgt gatatctcca ctgacgtaag    4980
ggatgacgca caatcccact atccttcgca agaccctcc tctatataag gaagttcatt    5040
tcatttggag aggacacggg ggactctaga ggatccccga tccctacagg gtaaatttct    5100
agtttttctc cttcattttc ttggttagga ccctttctc ttttattt ttgagcttt    5160 gatctttctt taaactgatc tatttttaa ttgattggtt atggtgtaaa tattacatag    5220
ctttaactga taatctgatt actttatttc gtgtgtctat gatgatgatg atagttacag    5280
aaccgtcgag ggggatcgcc cgggccatgg acccagaacg acgcccggcc gacatccgcc    5340
gtgccaccga ggcggacatg ccggcggtct gcaccatcgt caaccactac atcgagacaa    5400
gcacggtcaa cttccgtacc gagccgcagg aaccgcagga gtggacggac gacctcgtcc    5460
```

```
gtctgcggga gcgctatccc tggctcgtcg ccgaggtgga cggcgaggtc gccggcatcg   5520
cctacgcggg cccctggaag gcacgcaacg cctacgactg gacggccgag tcgaccgtgt   5580
acgtctcccc ccgccaccag cggacgggac tgggctccac gctctacacc cacctgctga   5640
agtccctgga ggcacagggc ttcaagagcg tggtcgctgt catcgggctg cccaacgacc   5700
cgagcgtgcg catgcacgag gcgctcggat atgcccccg cggcatgctg cgggcggccg    5760
gcttcaagca cgggaactgg catgacgtgg gtttctggca gctggacttc agcctgccgg   5820
taccgccccg tccggtcctg cccgtcaccg agatctgatc atttaaattg aaatcaccag   5880
tctctctcta caaatctatc tctctctata ataatgtgtg agtagttccc agataaggga   5940
attagggttc ttatagggtt tcgctcatgt gttgagcata taagaaaccc ttagtatgta   6000
tttgtatttg taaaatactt ctatcaataa aatttctaat tcctaaaacc aaaatccagt   6060
gggcgcgccg aattcagtac attaaaaacg tccgcaatgt gttattaagt tgtctaagcg   6120
tcaatttgtt tacaccacaa tatatcctgc caccagccag ccaacagctc cccgaccggc   6180
agctcggcac aaaatcacca ctcgatacag gcagcccatc agtccgggac ggcgtcagcg   6240
ggagagccgt tgtaaggcgg cagactttgc tcatgttacc gatgctattc ggaagaacg    6300 caactaagct gccgggtttg aaacacggat gatctcgcgg agggtagcat gttgattgta   6360
acgatgacag agcgttgctg cctgtgatca aatatcatct ccctcgcaga gatccgaatt   6420
atcagccttc ttattcattt ctcgcttaac cgtgacaggc tgtcgatctt gagaactatg   6480
ccgacataat aggaaatcgc tggataaagc cgctgaggaa gctgagtggc gctatttctt   6540
tagaagtgaa cgttgacgat cgtcgaccgt accccgatga attaattcgg acgtacgttc   6600
tgaacacagc tggatactta cttgggcgat tgtcatacat gacatcaaca atgtacccgt   6660
ttgtgtaacc gtctcttgga ggttcgtatg acactagtgg ttcccctcag cttgcgacta   6720
gatgttgagg cctaacattt tattagagag caggctagtt gcttagatac atgatcttca   6780
ggccgttatc tgtcagggca agcgaaaatt ggccatttat gacgaccaat gccccgcaga   6840
agctcccatc tttgccgcca tagacgccgc gcccccttt tggggtgtag aacatccttt    6900
tgccagatgt ggaaaagaag ttcgttgtcc cattgttggc aatgacgtag tagccggcga   6960
aagtgcgaga cccatttgcg ctatatataa gcctacgatt tccgttgcga ctattgtcgt   7020
aattggatga actattatcg tagttgctct cagagttgtc gtaatttgat ggactattgt   7080
cgtaattgct tatggagttg tcgtagttgc ttggagaaat gtcgtagttg gatggggagt   7140
agtcataggg aagacgagct tcatccacta aaacaattgg caggtcagca agtgcctgcc   7200
ccgatgccat cgcaagtacg aggcttagaa ccaccttcaa cagatcgcgc atagtcttcc   7260
ccagctctct aacgcttgag ttaagccgcg ccgcgaagcg gcgtcggctt gaacgaattg   7320
ttagacatta tttgccgact accttggtga tctcgccttt cacgtagtga acaaattctt   7380
ccaactgatc tgcgcgcgag gccaagcgat cttcttgtcc aagataagcc tgcctagctt   7440
caagtatgac gggctgatac tgggccggca ggcgctccat tgcccagtcg gcagcgacat   7500
ccttcggcgc gattttgccg gttactgcgc tgtaccaaat gcgggacaac gtaagcacta   7560
catttcgctc atcgccagcc cagtcgggcg gcgagttcca tagcgttaag gtttcattta   7620
gcgcctcaaa tagatcctgt tcaggaaccg gatcaaagag ttcctccgcc gctggaccta   7680
ccaaggcaac gctatgttct cttgcttttg tcagcaagat agccagatca atgtcgatcg   7740
tggctggctc gaagatacct gcaagaatgt cattgcgctc ccattctcca aattgcagtt   7800
cgcgcttagc tggataacgc cacggaatga tgtcgtcgtg cacaacaatg gtgacttcta   7860
```

```
cagcgcggag aatctcgctc tctccagggg aagccgaagt ttccaaaagg tcgttgatca    7920
aagctcgccg cgttgtttca tcaagcctta cggtcaccgt aaccagcaaa tcaatatcac    7980
tgtgtggctt caggccgcca tccactgcgg agccgtacaa atgtacggcc agcaacgtcg    8040
gttcgagatg gcgctcgatg acgccaacta cctctgatag ttgagtcgat acttcggcga    8100
tcaccgcttc cctcatgatg tttaactcct gaattaagcc gcgccgcgaa gcggtgtcgg    8160
cttgaatgaa ttgttaggcg tcatcctgtg ctcccgagaa ccagtaccag tacatcgctg    8220
tttcgttcga gacttgaggt ctagttttat acgtgaacag gtcaatgccg ccgagagtaa    8280
agccacattt tgcgtacaaa ttgcaggcag gtacattgtt cgtttgtgtc tctaatcgta    8340
tgccaaggag ctgtctgctt agtgcccact ttttcgcaaa ttcgatgaga ctgtgcgcga    8400
ctcctttgcc tcggtgcgtg tgcgacacaa caatgtgttc gatagaggct agatcgttcc    8460
atgttgagtt gagttcaatc ttcccgacaa gctcttggtc gatgaatgcg ccatagcaag    8520
cagagtcttc atcagagtca tcatccgaga tgtaatcctt ccggtagggg ctcacacttc    8580
tggtagatag ttcaaagcct tggtcggata ggtgcacatc gaacacttca cgaacaatga    8640
aatggttctc agcatccaat gtttccgcca cctgctcagg gatcaccgaa atcttcatat    8700
gacgcctaac gcctggcaca gcggatcgca aacctggcgc ggctttgggc acaaaaggcg    8760
tgacaggttt gcgaatccgt tgctgccact tgttaaccct tttgccagat ttggtaacta    8820
taatttatgt tagaggcgaa gtcttgggta aaaactggcc taaaattgct ggggatttca    8880
ggaaagtaaa catcacccttc cggctcgatg tctattgtag atatatgtag tgtatctact    8940
tgatcggggg atctgctgcc tcgcgcgttt cggtgatgac ggtgaaaacc tctgacacat    9000
gcagctcccg gagacggtca cagcttgtct gtaagcggat gccgggagca gacaagcccg    9060
tcagggcgcg tcagcgggtg ttggcgggtg tcgggcgca gccatgaccc agtcacgtag    9120
cgatagcgga gtgtatactg gcttaactat gcggcatcag agcagattgt actgagagtg    9180
caccatatgc ggtgtgaaat accgcacaga tgcgtaagga gaaaataccg catcaggcgc    9240
tcttccgctt cctcgctcac tgactcgctg cgctcggtcg ttcggctgcg gcgagcggta    9300
tcagctcact caaaggcggt aatacggtta tccacagaat cagggggataa cgcaggaaag    9360
aacatgtgag caaaaggcca gcaaaaggcc aggaaccgta aaaaggccgc gttgctggcg    9420
tttttccata ggctccgccc ccctgacgag catcacaaaa atcgacgctc aagtcagagg    9480
tggcgaaacc cgacaggact ataaagatac caggcgtttc cccctggaag ctccctcgtg    9540
cgctctcctg ttccgaccct gccgcttacc ggatacctgt ccgcctttct cccttcggga    9600
agcgtggcgc tttctcatag ctcacgctgt aggtatctca gttcggtgta ggtcgttcgc    9660
tccaagctgg gctgtgtgca cgaaccccc gttcagcccg accgctgcgc cttatccggt    9720
aactatcgtc ttgagtccaa cccggtaaga cacgacttat cgccactggc agcagccact    9780
ggtaacagga ttagcagagc gaggtatgta ggcggtgcta cagagttctt gaagtggtgg    9840
cctaactacg gctacactag aaggacagta tttggtatct gcgctctgct gaagccagtt    9900
accttcggaa aaagagttgg tagctcttga tccggcaaac aaaccaccgc tggtagcggt    9960
ggtttttttg tttgcaagca gcagattacg cgcagaaaaa aaggatctca agaagatcct    10020
ttgatctttt ctacggggtc tgacgctcag tggaacgaaa actcacgtta agggattttg    10080
gtcatgagat tatcaaaaag gatcttcacc tagatccttt taaattaaaa atgaagtttt    10140
aaatcaatct aaagtatata tgagtaaact tggtctgaca gttaccaatg cttaatcagt    10200
gaggcaccta tctcagcgat ctgtctattt cgttcatcca tagttgcctg actccccgtc    10260
```

```
gtgtagataa ctacgatacg ggagggctta ccatctggcc ccagtgctgc aatgataccg    10320
cgagacccac gctcaccggc tccagattta tcagcaataa accagccagc cggaagggcc    10380
gagcgcagaa gtggtcctgc aactttatcc gcctccatcc agtctattaa ttgttgccgg    10440
gaagctagag taagtagttc gccagttaat agtttgcgca acgttgttgc cattgctgca    10500
gggggggggg ggggggggtt ccattgttca ttccacggac aaaaacagag aaaggaaacg    10560
acagaggcca aaaagctcgc tttcagcacc tgtcgtttcc tttcttttca gagggtattt    10620
taaataaaaa cattaagtta tgacgaagaa gaacggaaac gccttaaacc ggaaaatttt    10680
cataaatagc gaaaacccgc gaggtcgccg ccccgtaacc tgtcggatca ccggaaagga    10740
cccgtaaagt gataatgatt atcatctaca tatcacaacg tgcgtggagg ccatcaaacc    10800
acgtcaaata atcaattatg acgcaggtat cgtattaatt gatctgcatc aacttaacgt    10860
aaaaacaact tcagacaata caaatcagcg acactgaata cggggcaacc tcatgtcccc    10920
cccccccccc ccctgcaggc atcgtggtgt cacgctcgtc gtttggtatg gcttcattca    10980
gctccggttc ccaacgatca aggcgagtta catgatcccc catgttgtgc aaaaaagcgg    11040
ttagctcctt cggtcctccg atcgttgtca gaagtaagtt ggccgcagtg ttatcactca    11100
tggttatggc agcactgcat aattctctta ctgtcatgcc atccgtaaga tgcttttctg    11160
tgactggtga gtactcaacc aagtcattct gagaatagta tatgcggcga ccgagttgct    11220
cttgcccggc gtcaacacgg gataataccg cgccacatag cagaacttta aaagtgctca    11280
tcattggaaa acgttcttcg gggcgaaaac tctcaaggat cttaccgctg ttgagatcca    11340
gttcgatgta acccactcgt gcacccaact gatcttcagc atctttact ttcaccagcg    11400 tttctgggtg agcaaaaaca ggaaggcaaa atgccgcaaa aaagggaata agggcgacac    11460
ggaaatgttg aatactcata ctcttccttt ttcaatatta ttgaagcatt tatcagggtt    11520
attgtctcat gagcggatac atatttgaat gtatttagaa aaataaacaa ataggggttc    11580
cgcgcacatt tccccgaaaa gtgccacctg acgtctaaga aaccattatt atcatgacat    11640
taacctataa aaataggcgt atcacgaggc cctttcgtct tcaagaattg gtcgacgatc    11700
ttgctgcgtt cggatatttt cgtggagttc cgccacaga cccggattga aggcgagatc    11760
cagcaactcg cgccagatca tcctgtgacg gaactttggc gcgtgatgac tggccaggac    11820
gtcggccgaa agagcgacaa gcagatcacg cttttcgaca gcgtcggatt tgcgatcgag    11880 gattttcgg cgctgcgcta cgtccgcgac gcgttgagg gatcaagcca cagcagccca    11940
ctcgaccttc tagccgaccc agacgagcca agggatcttt ttggaatgct gctccgtcgt    12000 caggcttttcc gacgtttggg tggttgaaca gaagtcatta tcgcacggaa tgccaagcac    12060
tcccgagggg aaccctgtgg ttggcatgca catacaaatg gacgaacgga taaaccttt    12120 cacgcccttt taaatatccg attattctaa taaacgctct tttctcttag gtttaccgc    12180 caatatatcc tgtcaaacac tgatagttta acctgaaggc gggaaacgac aatctgatca    12240
tgagcggaga attaagggag tcacgttatg accccgccg atgacgcggg acaagccgtt    12300
ttacgtttgg aactgacaga accgcaacgt tgaaggagcc actcagc                  12347
```

<210> SEQ ID NO 2
<211> LENGTH: 12096
<212> TYPE: DNA
<213> ORGANISM: Artificial
<220> FEATURE:
<223> OTHER INFORMATION: Plasmid for Agrobacterium

<400> SEQUENCE: 2

```
aagcttggcc ggccgtttaa actgcagcgt gacccggtcg tgcccctctc tagagataat    60
gagcattgca tgtctaagtt ataaaaaatt accacatatt tttttttgtca cacttgtttg   120
aagtgcagtt tatctatctt tatacatata tttaaacttt actctacgaa taatataatc   180
tatagtacta caataatatc agtgttttag agaatcatat aaatgaacag ttagacatgg   240
tctaaaggac aattgagtat tttgacaaca ggactctaca gttttatctt tttagtgtgc   300
atgtgttctc cttttttttt gcaaatagct tcacctatat aatacttcat ccattttatt   360
agtacatcca tttagggttt agggttaatg gttttatag actaattttt ttagtacatc    420
tattttattc tattttagcc tctaaattaa gaaaactaaa actctatttt agttttttta   480
tttaataatt tagatataaa atagaataaa ataaagtgac taaaaattaa acaaataccc   540
tttaagaaat taaaaaaact aaggaaacat ttttcttgtt tcgagtagat aatgccagcc   600
tgttaaacgc cgtcgacgag tctaacggac accaaccagc gaaccagcag cgtcgcgtcg   660
ggccaagcga agcagacggc acggcatctc tgtcgctgcc tctggacccc tctcgagagt   720
tccgctccac cgttggactt gctccgctgt cggcatccag aaattgcgtg gcggagcggc   780
agacgtgagc cggcacggca ggcggcctcc tcctcctctc acggcaccgg cagctacggg   840
ggattccttt cccaccgctc cttcgctttc ccttcctcgc ccgccgtaat aaatagacac   900
cccctccaca ccctctttcc ccaacctcgt gttgttcgga gcgcacacac acacaaccag   960
atctccccca aatccacccg tcggcacctc cgcttcaagg tacgccgctc gtcctccccc  1020
cccccccctc tctaccttct ctagatcggc gttccggtcc atggttaggg cccggtagtt  1080
ctacttctgt tcatgtttgt gttagatccg tgtttgtgtt agatccgtgc tgctagcgtt  1140
cgtacacgga tgcgacctgt acgtcagaca cgttctgatt gctaacttgc cagtgtttct  1200
ctttggggaa tcctgggatg gctctagccg ttccgcagac gggatcgatt tcatgatttt  1260
ttttgtttcg ttgcataggg tttggttttgc ccttttcctt tatttcaata tatgccgtgc  1320
acttgtttgt cgggtcatct tttcatgctt ttttttgtct tggttgtgat gatgtggtct  1380
ggttgggcgg tcgttctaga tcggagtaga attctgtttc aaactacctg gtggatttat  1440
taattttgga tctgtatgtg tgtgccatac atattcatag ttacgaattg aagatgatgg  1500
atggaaatat cgatctagga taggtataca tgttgatgcg ggttttactg atgcatatac  1560
agagatgctt tttgttcgct tggttgtgat gatgtggtgt ggttgggcgg tcgttcattc  1620
gttctagatc ggagtagaat actgtttcaa actacctggt gtatttatta attttggaac  1680
tgtatgtgtg tgtcatacat cttcatagtt acgagtttaa gatggatgga aatatcgatc  1740
taggataggt atacatgttg atgtgggttt tactgatgca tatacatgat ggcatatgca  1800
gcatctattc atatgctcta accttgagta cctatctatt ataataaaca agtatgtttt  1860
ataattattt tgatcttgat atacttggat gatggcatat gcagcagcta tatgtggatt  1920
tttttagccc tgccttcata cgctatttat ttgcttggta ctgtttcttt tgtcgatgct  1980
caccctgttg tttggtgtta cttctgcagg tcgactctag attaattaag ttatcacaag  2040
tttgtacaaa aaagcaggct catttaactt taagaaggag atatatacca tggtccgtcc  2100
tgtagaaacc ccaacccgtg aaatcaaaaa actcgacggc ctgtgggcat tcagtctgga  2160
tcgcgaaaac tgtggaattg atcagcgttg gtgggaaagc gcgttacaag aaagccgggc  2220
aattgctgtg ccaggcagtt ttaacgatca gttcgccgat gcagatattc gtaattatgc  2280
gggcaacgtc tggtatcagc gcgaagtctt tataccgaaa ggttgggcag ccagcgtat   2340
cgtgctgcgt ttcgatgcgg tcactcatta cggcaaagtg tgggtcaata atcaggaagt  2400
```

```
gatggagcat cagggcggct atacgccatt tgaagccgat gtcacgccgt atgttattgc   2460
cgggaaaagt gtacgtatca ccgtttgtgt gaacaacgaa ctgaactggc agactatccc   2520
gccgggaatg tgattaccg acgaaaacgg caagaaaaag cagtcttact tccatgattt    2580
ctttaactat gccggaatcc atcgcagcgt aatgctctac accacgccga cacctgggt    2640
ggacgatatc accgtggtga cgcatgtcgc gcaagactgt aaccacgcgt ctgttgactg   2700
gcaggtggtg gccaatggtg atgtcagcgt tgaactgcgt gatgcggatc aacaggtggt   2760
tgcaactgga caaggcacta gcgggacttt gcaagtggtg aatccgcacc tctggcaacc   2820
gggtgaaggt tatctctatg aactgtgcgt cacagccaaa agccagacag agtgtgatat   2880
ctacccgctt cgcgtcggca tccggtcagt ggcagtgaag ggcgaacagt tcctgattaa   2940
ccacaaaccg ttctacttta ctggctttgg tcgtcatgaa gatgcggact acgtggcaa   3000
aggattcgat aacgtgctga tggtgcacga ccacgcatta atggactgga ttggggccaa   3060
ctcctaccgt acctcgcatt acccttacgc tgaagagatg ctcgactggg cagatgaaca   3120
tggcatcgtg gtgattgatg aaactgctgc tgtcggcttt aacctctctt taggcattgg   3180
tttcgaagcg ggcaacaagc cgaaagaact gtacagcgaa gaggcagtca acggggaaac   3240
tcagcaagcg cacttacagg cgattaaaga gctgatagcg cgtgacaaaa accacccaag   3300
cgtggtgatg tggagtattg ccaacgaacc ggatacccgt ccgcaaggtg cacgggaata   3360
tttcgcgcca ctggcggaag caacgcgtaa actcgacccg acgcgtccga tcacctgcgt   3420
caatgtaatg ttctgcgacg ctcacaccga taccatcagc gatctctttg atgtgctgtg   3480
cctgaaccgt tattacggat ggtatgtcca agcggcgat ttggaaacgg cagagaaggt    3540
actggaaaaa gaacttctgg cctggcagga gaaactgcat cagccgatta tcatcaccga   3600
atacggcgtg gatacgttag ccgggctgca ctcaatgtac accgacatgt ggagtgaaga   3660
gtatcagtgt gcatggctgg atatgtatca ccgcgtcttt gatcgcgtca cgccgtcgt    3720
cggtgaacag gtatggaatt cgccgatttt tgcgacctcg caaggcatat tgcgcgttgg   3780
cggtaacaag aaagggatct tcactcgcga ccgcaaaccg aagtcggcgg cttttctgct   3840
gcaaaaacgc tggactggca tgaacttcgg tgaaaaaccg cagcagggag gcaaacaata   3900
atacccagct ttcttgtaca agtggtgat aacagatcgt tcaaacattt ggcaataaag    3960
tttcttaaga ttgaatcctg ttgccggtct tgcgatgatt atcatataat ttctgttgaa   4020
ttacgttaag catgtaataa ttaacatgta atgcatgacg ttatttatga gatgggtttt   4080
tatgattaga gtcccgcaat tatacattta atacgcgata gaaaacaaaa tatagcgcgc   4140
aaactaggat aaattatcgc gcgcggtgtc atctatgtta ctagatccga tgataagctg   4200
tcaaacatga ggcgatcgcc ccgagcaata atctccagga aatcaaatac cttcccaaga   4260
aggttaaaga tgcagtcaaa agattcagga ctaactgcat caagaacaca gagaaagata   4320
tatttctcaa gatcagaagt actattccag tatggacgat tcaaggcttg cttcacaaac   4380
caaggcaagt aatagagatt ggagtctcta aaaaggtagt tcccactgaa tcaaaggcca   4440
tggagtcaaa gattcaaata gaggacctaa cagaactcgc cgtaaagact ggcgaacagt   4500
tcatacagag tctcttacga ctcaatgaca agaagaaaat cttcgtcaac atggtggagc   4560
acgacacact tgtctactcc aaaaatatca agatacagt ctcagaagac caagggcaa     4620
ttgagacttt tcaacaaagg gtaatatccg gaaacctcct cggattccat tgcccagcta   4680
tctgtcactt tattgtgaag atagtggaaa aggaaggtgg ctcctacaaa tgccatcatt   4740
gcgataaagg aaaggccatc gttgaagatg cctctgccga cagtggtccc aaagatggac   4800
```

```
ccccacccac gaggagcatc gtggaaaaag aagacgttcc aaccacgtct tcaaagcaag      4860
tggattgatg tgatatctcc actgacgtaa gggatgacgc acaatcccac tatccttcgc      4920
aagacccttc ctctatataa ggaagttcat ttcatttgga gagaacacgg gggactctag      4980
aggatccccg atccctacag ggtaaatttc tagtttttct ccttcatttt cttggttagg      5040
acccttttct cttttatttt ttttgagctt tgatctttct ttaaactgat ctatttttta      5100
attgattggt tatggtgtaa atattacata gctttaactg ataatctgat tactttattt      5160
cgtgtgtcta tgatgatgat gatagttaca gaaccgtcga gggggatcca ccatgccttt      5220
gtctcaagaa gaatccaccc tcattgaaag agcaacggct acaatcaaca gcatcccat      5280 ctctgaagac tacagcgtcg ccagcgcagc tctctctagc gacggccgca tcttcactgg      5340
tgtcaatgta tatcatttta ctgggggacc ttgtgcagaa ctcgtggtgc tgggcactgc      5400
tgctgctgcg gcagctggca acctgacttg tatcgtcgcg atcggaaatg agaacagggg      5460
catcttgagc ccctgcggac ggtgccgaca ggtgcttctc gatctgcatc ctgggatcaa      5520
agccatagtg aaggacagtg atggacagcc gacggcagtt gggattcgtg aattgctgcc      5580
ctctggttat gtgtgggagg gctaagcaca tttaaattga aatcaccagt ctctctctac      5640
aaatctatct ctctctataa taatgtgtga gtagttccca gataagggaa ttagggttct      5700
tatagggttt cgctcatgtg ttgagcatat aagaaaccct tagtatgtat ttgtatttgt      5760
aaaatacttc tatcaataaa atttctaatt cctaaaacca aaatccagtg ggcgcgccga      5820
attcagtaca ttaaaaacgt ccgcaatgtg ttattaagtt gtctaagcgt caatttgttt      5880
acaccacaat atatcctgcc accagccagc caacagctcc ccgaccggca gctcggcaca      5940
aaatcaccac tcgatacagg cagcccatca gtccgggacg cgtcagcgg gagagccgtt      6000 gtaaggcggc agactttgct catgttaccg atgctattcg gaagaacggc aactaagctg      6060
ccgggtttga aacacggatg atctcgcgga gggtagcatg ttgattgtaa cgatgacaga      6120
gcgttgctgc ctgtgatcaa atatcatctc cctcgcagag atccgaatta tcagccttct      6180
tattcatttc tcgcttaacc gtgacaggct gtcgatcttg agaactatgc cgacataata      6240
ggaaatcgct ggataaagcc gctgaggaag ctgagtggcg ctatttcttt agaagtgaac      6300
gttgacgatc gtcgaccgta ccccgatgaa ttaattcgga cgtacgttct gaacacagct      6360
ggatacttac ttgggcgatt gtcatacatg acatcaacaa tgtacccgtt tgtgtaaccg      6420
tctcttggag gttcgtatga cactagtggt tcccctcagc ttgcgactag atgttgaggc      6480
ctaacatttt attagagagc aggctagttg cttagataca tgatcttcag gccgttatct      6540
gtcagggcaa gcgaaaattg gccatttatg acgaccaatg ccccgcagaa gctcccatct      6600
ttgccgccat agacgccgcg ccccccttt ggggtgtaga acatccttt gccagatgtg      6660 gaaaagaagt tcgttgtccc attgttggca atgacgtagt agccggcgaa agtgcgagac      6720
ccatttgcgc tatatataag cctacgattt ccgttgcgac tattgtcgta attggatgaa      6780
ctattatcgt agttgctctc agagttgtcg taatttgatg gactattgtc gtaattgctt      6840
atggagttgt cgtagttgct tggagaaatg tcgtagttgg atggggagta gtcataggga      6900 agacagagctt catccactaa aacaattggc aggtcagcaa gtgcctgccc cgatgccatc      6960
gcaagtacga ggcttagaac caccttcaac agatcgcgca tagtcttccc cagctctcta      7020
acgcttgagt taagccgcgc cgcgaagcgg cgtcggcttg aacgaattgt tagacattat      7080
ttgccgacta ccttggtgat ctcgcctttc acgtagtgaa caaattcttc caactgatct      7140
gcgcgcgagg ccaagcgatc ttcttgtcca agataagcct gcctagcttc aagtatgacg      7200
```

```
ggctgatact gggccggcag gcgctccatt gcccagtcgg cagcgacatc cttcggcgcg   7260
attttgccgg ttactgcgct gtaccaaatg cgggacaacg taagcactac atttcgctca   7320
tcgccagccc agtcgggcgg cgagttccat agcgttaagg tttcatttag cgcctcaaat   7380
agatcctgtt caggaaccgg atcaaagagt tcctccgccg ctggacctac caaggcaacg   7440
ctatgttctc ttgcttttgt cagcaagata gccagatcaa tgtcgatcgt ggctggctcg   7500
aagatacctg caagaatgtc attgcgctgc cattctccaa attgcagttc gcgcttagct   7560
ggataacgcc acggaatgat gtcgtcgtgc acaacaatgg tgacttctac agcgcggaga   7620
atctcgctct ctccagggga agccgaagtt ccaaaaggt cgttgatcaa agctcgccgc    7680
gttgtttcat caagccttac ggtcaccgta accagcaaat caatatcact gtgtggcttc   7740
aggccgccat ccactgcgga gccgtacaaa tgtacggcca gcaacgtcgg ttcgagatgg   7800
cgctcgatga cgccaactac ctctgatagt tgagtcgata cttcggcgat caccgcttcc   7860
ctcatgatgt ttaactcctg aattaagccg cgccgcgaag cggtgtcggc ttgaatgaat   7920
tgttaggcgt catcctgtgc tcccgagaac cagtaccagt acatcgctgt ttcgttcgag   7980
acttgaggtc tagtttttata cgtgaacagg tcaatgccgc cgagagtaaa gccacatttt   8040
gcgtacaaat tgcaggcagg tacattgttc gtttgtgtct ctaatcgtat gccaaggagc   8100
tgtctgctta gtgcccactt tttcgcaaat tcgatgagac tgtgcgcgac tcctttgcct   8160
cggtgcgtgt gcgacacaac aatgtgttcg atagaggcta gatcgttcca tgttgagttg   8220
agttcaatct tcccgacaag ctcttggtcg atgaatgcgc catagcaagc agagtcttca   8280
tcagagtcat catccgagat gtaatccttc cggtaggggc tcacacttct ggtagatagt   8340
tcaaagcctt ggtcggatag gtgcacatcg aacacttcac gaacaatgaa atggttctca   8400
gcatccaatg tttccgccac ctgctcaggg atcaccgaaa tcttcatatg acgcctaacg   8460
cctggcacag cggatcgcaa acctggcgcg gctttgggca caaaggcgt gacaggtttg    8520 cgaatccgtt gctgccactt gttaacccct ttgccagatt tggtaactat aatttatgtt   8580
agaggcgaag tcttgggtaa aaactggcct aaaattgctg gggatttcag gaaagtaaac   8640
atcaccttcc ggctcgatgt ctattgtaga tatatgtagt gtatctactt gatcggggga   8700
tctgctgcct cgcgcgtttc ggtgatgacg gtgaaaacct ctgacacatg cagctcccgg   8760
agacggtcac agcttgtctg taagcggatg ccgggagcag acaagcccgt cagggcgcgt   8820
cagcgggtgt tggcggtgt cggggcgcag ccatgaccca gtcacgtagc gatagcggag     8880
tgtatactgg cttaactatg cggcatcaga gcagattgta ctgagagtgc accatatgcg   8940
gtgtgaaata ccgcacagat gcgtaaggag aaaataccgc atcaggcgct cttccgcttc   9000
ctcgctcact gactcgctgc gctcggtcgt tcggctgcgg cgagcggtat cagctcactc   9060
aaaggcggta atacggttat ccacagaatc agggggataac gcaggaaaga acatgtgagc   9120
aaaaggccag caaaaggcca ggaaccgtaa aaaggccgcg ttgctggcgt ttttccatag   9180
gctccgcccc cctgacgagc atcacaaaaa tcgacgctca agtcagaggt ggcgaaaccc   9240
gacaggacta taaagatacc aggcgtttcc ccctggaagc tccctcgtgc gctctcctgt   9300
tccgaccctg ccgcttaccg gatacctgtc cgcctttctc ccttcgggaa gcgtggcgct   9360
ttctcatagc tcacgctgta ggtatctcag ttcggtgtag tcgttcgct ccaagctggg     9420 ctgtgtgcac gaacccccccg ttcagcccga ccgctgcgcc ttatccggta actatcgtct   9480
tgagtccaac ccggtaagac acgacttatc gccactggca gcagccactg gtaacaggat   9540
tagcagagcg aggtatgtag gcggtgctac agagttcttg aagtggtggc ctaactacgg   9600
```

```
ctacactaga aggacagtat ttggtatctg cgctctgctg aagccagtta ccttcggaaa   9660
aagagttggt agctcttgat ccggcaaaca aaccaccgct ggtagcggtg ttttttttgt   9720
ttgcaagcag cagattacgc gcagaaaaaa aggatctcaa gaagatcctt tgatcttttc   9780
tacggggtct gacgctcagt ggaacgaaaa ctcacgttaa gggattttgg tcatgagatt   9840
atcaaaaagg atcttcacct agatcctttt aaattaaaaa tgaagtttta atcaatcta   9900 aagtatatat gagtaaactt ggtctgacag ttaccaatgc ttaatcagtg aggcacctat   9960
ctcagcgatc tgtctatttc gttcatccat agttgcctga ctccccgtcg tgtagataac  10020
tacgatacgg gagggcttac catctggccc cagtgctgca atgataccgc gagacccacg  10080
ctcaccggct ccagatttat cagcaataaa ccagccagcc ggaagggccg agcgcagaag  10140
tggtcctgca actttatccg cctccatcca gtctattaat tgttgccggg aagctagagt  10200
aagtagttcg ccagttaata gtttgcgcaa cgttgttgcc attgctgcag ggggggggg   10260 ggggggttc cattgttcat tccacggaca aaaacagaga aaggaaacga cagaggccaa  10320
aaagctcgct ttcagcacct gtcgtttcct ttcttttcag agggtatttt aaataaaaac  10380
attaagttat gacgaagaag aacgaaaacg ccttaaaccg gaaaatttc ataaatagcg  10440 aaaacccgcg aggtcgccgc cccgtaacct gtcggatcac cggaaaggac ccgtaaagtg  10500
ataatgatta tcatctacat atcacaacgt gcgtggaggc catcaaacca cgtcaaataa  10560
tcaattatga cgcaggtatc gtattaattg atctgcatca acttaacgta aaacaactt   10620 cagacaatac aaatcagcga cactgaatac ggggcaacct catgtccccc cccccccc    10680 cctgcaggca tcgtggtgtc acgctcgtcg tttggtatgg cttcattcag ctccggttcc  10740
caacgatcaa ggcgagttac atgatccccc atgttgtgca aaaaagcggt tagctccttc  10800
ggtcctccga tcgttgtcag aagtaagttg gccgcagtgt tatcactcat ggttatggca  10860
gcactgcata attctcttac tgtcatgcca tccgtaagat gcttttctgt gactggtgag  10920
tactcaacca agtcattctg agaatagtgt atgcggcgac cgagttgctc ttgcccggcg  10980
tcaacacggg ataataccgc gccacatagc agaactttaa aagtgctcat cattggaaaa  11040
cgttcttcgg ggcgaaaact ctcaaggatc ttaccgctgt tgagatccag ttcgatgtaa  11100
cccactcgtg cacccaactg atcttcagca tcttttactt tcaccagcgt ttctgggtga  11160
gcaaaaacag gaaggcaaaa tgccgcaaaa aagggaataa gggcgacacg gaaatgttga  11220
atactcatac tcttcctttt tcaatattat tgaagcattt atcagggtta ttgtctcatg  11280
agcggataca tatttgaatg tatttagaaa aataaacaaa taggggttcc gcgcacattt  11340
ccccgaaaag tgccacctga cgtctaagaa accattatta tcatgacatt aacctataaa  11400
aataggcgta tcacgaggcc ctttcgtctt caagaattgg tcgacgatct tgctgcgttc  11460
ggatattttc gtggagttcc cgccacagac ccggattgaa ggcgagatcc agcaactcgc  11520
gccagatcat cctgtgacgg aactttggcg cgtgatgact ggccaggacg tcggccgaaa  11580
gagcgacaag cagatcacgc ttttcgacag cgtcggattt gcatcgagg attttcggc    11640 gctgcgctac gtccgcgacc gcgttgaggg atcaagccac agcagccac tcgaccttct   11700 agccgaccca gacgagccaa gggatctttt tggaatgctg ctccgtcgtc aggctttccg  11760
acgtttgggt ggttgaacag aagtcattat cgcacggaat gccaagcact cccgagggga  11820
accctgtggt tggcatgcac atacaaatgg acgaacggat aaaccttttc acgccctttt  11880
aaatatccga ttattctaat aaacgctctt ttctcttagg tttacccgcc aatatatcct  11940
gtcaaacact gatagtttaa cctgaaggcg ggaaacgaca atctgatcat gagcggagaa  12000
```

```
ttaagggagt cacgttatga cccccgccga tgacgcggga caagccgttt tacgtttgga    12060
actgacagaa ccgcaacgtt gaaggagcca ctcagc                              12096
```